(12) United States Patent
Dhamankar et al.

(10) Patent No.: US 8,669,379 B2
(45) Date of Patent: Mar. 11, 2014

(54) MICROBIAL PRODUCTION OF 3,4-DIHYDROXYBUTYRATE (3,4-DHBA), 2,3-DIHYDROXYBUTYRATE (2,3-DHBA) AND 3-HYDROXYBUTYROLACTONE (3-HBL)

(75) Inventors: Himanshu Hemant Dhamankar, Cambridge, MA (US); Collin Hunter Martin, North Wales, PA (US); Kristala Lanett Jones Prather, Milton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/404,993

(22) Filed: Feb. 24, 2012

(65) Prior Publication Data

US 2012/0226055 A1 Sep. 6, 2012

Related U.S. Application Data

(60) Provisional application No. 61/446,998, filed on Feb. 25, 2011.

(51) Int. Cl.
| | | |
|---|---|---|
| C07D 307/00 | (2006.01) | |
| C07C 59/10 | (2006.01) | |
| C12P 17/04 | (2006.01) | |
| C12P 7/42 | (2006.01) | |
| C12N 1/20 | (2006.01) | |
| C12N 1/00 | (2006.01) | |
| C12N 5/00 | (2006.01) | |
| C12N 5/07 | (2010.01) | |
| C12N 5/04 | (2006.01) | |
| C12N 15/74 | (2006.01) | |

(52) U.S. Cl.
USPC ........... 549/313; 562/587; 435/126; 435/146; 435/252.3; 435/254.1; 435/254.11; 435/254.2; 435/325; 435/348; 435/419; 435/471

(58) Field of Classification Search
USPC ........ 549/313; 562/587; 435/126, 146, 252.3, 435/254.1, 254.11, 254.2, 325, 348, 419, 435/471
See application file for complete search history.

(56) References Cited

U.S. PATENT DOCUMENTS

| | | |
|---|---|---|
| 5,808,107 A | 9/1998 | Hollingsworth |
| 8,361,760 B2 | 1/2013 | Martin et al. |
| 2009/0155867 A1* | 6/2009 | Soucaille ..................... 435/135 |

FOREIGN PATENT DOCUMENTS

| | | | |
|---|---|---|---|
| WO | WO 2007/140816 A1 | 12/2007 | |
| WO | WO 2008/062996 A1 | 5/2008 | |
| WO | WO 2009/145840 A2 | 12/2009 | |
| WO | WO 2010/101651 A1 * | 9/2010 | ................ C12R 1/19 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Kisselev L., Polypeptide release factors in prokaryotes and eukaryotes: same function, different structure. Structure, 2002, vol. 10: 8-9.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., a single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
PCT/US2010/000674, Jun. 18, 2010, International Search Report and Written Opinion.
PCT/US2010/000674, Sep. 15, 2011, International Preliminary Report on Patentability.
PCT/US2012/026577, Aug. 8, 2012, International Search Report and Written Opinion.
PCT/US2012/026577, Sep. 6, 2013, International Preliminary Report on Patentability.
GENBANK Submission; NCBI; Accession No. AAN67665.1; Nelson et al.; Mar. 5, 2010.
Boynton et al., Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824. J Bacteriol. Jun. 1996;178(11):3015-24.
Boynton et al., Cloning, sequencing, and expression of genes encoding phosphotransacetylase and acetate kinase from Clostridium acetobutylicum ATCC 824. Appl Environ Microbiol. Aug. 1996;62(8):2758-66.
Chen et al., Microbial production and applications of chiral hydroxyalkanoates. Appl Microbiol Biotechnol. Jun. 2005;67(5):592-9. Epub Feb. 8, 2005.
Chiba et al., A synthetic approach to (+)-thienamycin from methyl (r)-3-hydroxybutanoate. a new entry to (3r, 4r)-3-[(r)-1-hydroxyethyl[-4-acetoxy-2-azetidinone. Chem Lett. 1985;14(5):651-4.

(Continued)

Primary Examiner — Ganapathirama Raghu
(74) Attorney, Agent, or Firm — Wolf, Greenfield & Sacks, P.C.

(57) ABSTRACT

The invention relates to recombinant cells and their use in the production of 3,4-dihydroxybutyrate, 2,3-dihydroxybutyrate and 3-hydroxybutyrolactone.

22 Claims, 26 Drawing Sheets

(56) References Cited

OTHER PUBLICATIONS

Dhamankar et al., Biosynthesis of 3-hydroxy-g-butyrolactone and 3,4-dihydroxybutyric acid in *Escherichia coli* from glucose as a sole feedstock. Am Chem Soc. Mar. 30, 2011;241:358.

Gao et al., Enhanced production of D-(−)-3-hydroxybutyric acid by recombinant *Escherichia coli*. FEMS Microbiol Lett. Jul. 16, 2002;213(1):59-65.

Greenler et al., Isolation, characterization and sequence analysis of a full-length cDNA clone encoding NADH-dependent hydroxypyruvate reductase from cucumber. Plant Mol Biol. Aug. 1989;13(2): 139-50.

Huisman et al., Metabolism of poly(3-hydroxyalkanoates) (PHAs) by *Pseudomonas oleovorans*. Identification and sequences of genes and function of the encoded proteins in the synthesis and degradation of PHA. J Biol Chem. Feb. 5, 1991;266(4):2191-8.

Kim et al., Crystal structure of HIV-1 protease in complex with VX-478, a potent and orally bioavailable inhibitor of the enzyme. J Am Chem Soc. 1995;117(3):1181-2.

Lee et al., A chemoenzymatic approach to the synthesis of enantiomerically pure (S)-3-hydroxy-gamma-butyrolactone. Appl Microbiol Biotechnol. Jun. 2008;79(3):355-62. Epub May 1, 2008.

Lee et al., Biosynthesis of enantiopure (S)-3-hydroxybutyric acid in metabolically engineered *Escherichia coli*. Appl Microbiol Biotechnol. Jun. 2008;79(4):633-41. Epub May 7, 2008.

Lee et al., Fermentative butanol production by *Clostridia*. Biotechnol Bioeng. Oct. 1, 2008;101(2):209-28.

Lee et al., Production of chiral and other valuable compounds from microbial polyesters. Biopolymers, polyesters III. Eds. Dio et al. Wiley-VCH. Weinheim. 2002. p. 375-87.

Lee et al., Uses and production of chiral 3-hydroxy-gamma-butyrolactones and structurally related chemicals. Appl Microbiol Biotechnol. Oct. 2009;84(5):817-28. Epub Aug. 4, 2009.

Liu et al., A novel genetically engineered pathway for synthesis of poly(hydroxyalkanoic acids) in *Eschericia coli*. Appl Environ Microbiol. Feb. 2000;66(2):739-43.

Liu et al., Exploitation of butyrate kinase and phosphotransbutyrlase from *Clostridium acebutylicum* for the in vitro biosynthesis of poly(hydroxyalkanoic acid). Appl Microbiol Biotechnol. May 2000;53(5):545-52.

Liu et al., Microbial production of R-3-hydroxybutyric acid by recominant *E. coli* harboring genes of phbA, phbB, and tesB. Appl Microbiol Biotechnol. Sep. 2007;76(4):811-8. Epub Jul. 4, 2007.

Martin et al., High-titer production of monomeric hydroxyvalerates from levulinic acid in *Pseudomonas putida*. J Biotechnol. Jan. 1, 2009;139(1):61-7. Epub Sep. 25, 2008.

Naggert et al., Cloning, sequencing, and characterization of *Escherichia coli* thioesterase II. J Biol Chem. Jun. 15, 1991;266(17):11044-50.

Nuñez et al., Biochemical characterization of the 2-ketoacid reducatases encoded by ycdW and yiaE genes in *Escherichia coli*. Biochem J. Mar. 15, 2001;354(Pt 3):707-15.

Park et al., Preparation of optically active β-amino acids from microbial polyester polyhydroxyalkanoates. J Chem Res. Nov. 1, 2001;(11):498-9.

Peoples et al., Poly-beta-hydroxybutyrate biosynthesis in *Alcaligenes eutrophus* H16. Characterization of the genes encoding beta-ketothiolase and acetoacetyl-CoA reducatase. J Biol Chem. Sep. 15, 1989;264(26):15293-7.

Schubert et al., Cloning of the *Alcaligenes eutrophus* genes for synthesis of poly-beta-hydroxybutyric acid (PHB) and synthesis of PHB in *Escherichia coli*. J Bacteriol. Dec. 1998;170(12):5837-47.

Schweiger et al., On the dehydration of (R)-lactate in the fermentation of alanine to propionate by *Clostridium propionicum*. FEBS Lett. Jun. 4, 1984;171(1):79-84.

Seebach et al., From the biopolymer PHB to biological investigations of unnatural β- and γ-peptides. Chimia. 2001;55:345-53.

Slater et al., Multiple beta-ketothiolases mediate poly(beta-hydroxyalkanoate) copolymer synthesis in *Ralstonia eutropha*. J Bacteriol. Apr. 1998;180(8):1979-87.

Stim-Herndon et al., Characterization of an acetyl-CoA C-acetyltransferase (thiolase) gene from *Clostridium acetobutylicum* ATCC 824. Gene. Feb. 27, 1995;154(1):81-5.

Suriyamongkol et al., Biotechnological approaches for the production of polyhydroxyalkanoates in microorganisms and plants—a review. Biotechnol Adv. Mar.-Apr. 2007;25(2):148-75. Epub Nov. 20, 2006.

Taguchi et al., A microbial factory for lactate-based polyesters using a lactate-polymerizing enzyme. Proc Natl Acad Sci U S A. Nov. 11, 2008;105(45):17323-7. Epub Oct. 31, 2008.

Tseng et al., Metabolic engineering of *Escherichia coli* for enhanced production of (R)- and (S)-3-hydroxybutyrate. Appl Environ Microbiol. May 2009;75(10):3137-45. Epub Mar. 20, 2009.

Wang et al., Direct Conversion of (S)-3-Hydroxy-gamma-butyrolactone to Chiral Three-Carbon Building Blocks. J Org Chem. Feb. 5, 1999;64(3):1036-1038.

Wang et al., Synthetic routes to 1-carnitine and 1-gamma-amino-beta-hydroxybutyric acid from (S)-3-hydroxybutyrolactone by functional group priority switching. Tetrahedron: Asymmetry. May 21, 1999;10(10):1895-901.

Werpy et al., Top value added chemicals from biomass, vol. 1: results of screening for potential candidates from sugars and synthesis gas. Department of Energy, Oak Ridge, TN. Aug. 2004.

Williams et al., Biosynthetic thiolase from *Zoogloea ramigera*. Mutagenesis of the putative active-site base Cys-378 to Ser-378 changes the partitioning of the acetyl S-enzyme intermediate. J Biol Chem. Aug. 15, 1992;267(23):16041-3.

Yang et al., Biosynthesis of polylactic acid and its copolymers using evolved propionate CoA transferase and PHA synthase. Biotechnol Bioeng. Jan. 1, 2010;105(1):150-60.

Yasohara et al., Molecular cloning and overexpression of the gene encoding an NADPH-dependent carbonyl reductase from *Candida magnoliae*, involved in stereoselective reduction of ethyl 4-chloro-3-oxobutanoate. Biosci Biotechnol Biochem. Jul. 2000;64(7):1430-6.

* cited by examiner 2,2-D2-glycolic acid 3,4-DHBA (labeled) ammonium adduct
m/z = 140.1

2,3-DHBA (labeled) ammonium adduct
m/z = 139.1

MICROBIAL PRODUCTION OF 3,4-DIHYDROXYBUTYRATE (3,4-DHBA), 2,3-DIHYDROXYBUTYRATE (2,3-DHBA) AND 3-HYDROXYBUTYROLACTONE (3-HBL)

RELATED APPLICATIONS

This application claims the benefit under 35 U.S.C. §119 (e) of U.S. Provisional Application Ser. No. 61/446,998, entitled "MICROBIAL PRODUCTION OF 3,4-DIHYDROXYBUTYRATE (DHBA) AND 3-HYDROXYBUTYROLACTONE (3-HBL)," filed on Feb. 25, 2011, which is herein incorporated by reference in its entirety.

GOVERNMENT INTEREST

This invention was made with government support under Grant No. EEC0540879 awarded by the National Science Foundation. The government has certain rights in this invention.

FIELD OF THE INVENTION

The invention relates to the production of 3,4-dihydroxybutyrate, 2,3-dihydroxybutyrate and 3-hydroxybutyrolactone through recombinant gene expression.

BACKGROUND INFORMATION 3,4-dihydroxybutyrate (3,4-DHBA), 2,3-dihydroxybutyrate (2,3-DHBA) and 3-hydroxybutyrolactone (3-HBL) are highly useful chiral intermediates that can be used to synthesize statin-class drugs like CRESTOR® and LIPITOR®, carnitine, and other fine chemicals. The annual market for statin drugs was estimated to be $10-15 billion in 2003 and 2004, while the annual demand for carnitine (which is used as a vitamin supplement) is estimated to be several hundred metric tons. 3,4-DHBA and 3-HBL can also be readily derivatized into valuable compounds like carnitine, which has an approximate $5 per gram cost and is used as a vitamin and nutritional supplement.

Currently DHBA is not commercially available, while 3-HBL costs $30-100 per gram. The high cost and low availability of these compounds increases the costs of statin drugs. Existing methods for the synthesis of DHBA and 3-HBL rely on crude, harsh chemical synthetic means, such as the harsh reduction of malic acid or the breakdown of various hexose sugars with acid. Such chemical synthetic methods produce several byproducts, necessitating the extensive purification of the DHBA or 3-HBL product.

SUMMARY OF INVENTION

Described herein are efficient biological methods for producing 3,4-dihydroxybutyrate (3,4-DHBA), 2,3-dihydroxybutyrate (2,3-DHBA) and 3-hydroxybutyrolactone (3-HBL) in cells such as E. coli cells. Methods involve integration of pathways for glycolate synthesis with pathways for synthesis of 3,4-DHBA, 2,3-DHBA and 3-HBL, leading to efficient and cost-effective production of 3,4-DHBA, 2,3-DHBA and 3-HBL from simple fermentable sugars as a sole feedstock.

Aspects of the invention relate to cells that overexpress a ycdW gene, an aceA gene, and an aceK gene, and that recombinantly expresses a pct gene, at least one of a phaA, thil, atoB or bktB gene, and at least one of a phaB or hbd gene. In some embodiments, the cell has reduced or eliminated expression of an iclR gene, an aceB gene and a gcl gene relative to a wild type cell. In some embodiments, the cell further recombinantly expresses a tesB gene. In some embodiments, overexpression of ycdW, aceA and aceK, and recombinant expression of pct, at least one of phaA, thil, atoB or bktB, and at least one of phaB or hbd, is induced through at least two independently inducible expression systems.

Aspects of the invention involve recombinant cells. The cell can be a bacterial cell, a fungal cell (including a yeast cell), a plant cell, an insect cell or an animal cell. In some embodiments, the cell is a bacterial cell such as an *Escherichia coli* cell.

In some embodiments, the cell endogenously expresses ycdW, aceA, and/or aceK, and endogenous expression of ycdW, aceA, and/or aceK is increased through modification of the gene(s) and/or their promoter(s) and/or their ribosome binding sites (RBSs). In some embodiments, ycdW, aceA, and/or aceK is expressed from a plasmid. In some embodiments, one or more copies of ycdW, aceA, and/or aceK are integrated into the genome of the cell. In some embodiments, one or more of pct, phaA, thil, atoB, bktB, phaB or hbd is expressed from a plasmid. In some embodiments, one or more of pct, phaA, thil, atoB, bktB, phaB or hbd is integrated into the genome of the cell.

In some embodiments, the ycdW, aceA and/or aceK gene(s) is an *Escherichia coli* gene, such as an *Escherichia coli* K12 gene. In some embodiments, the phaA, bktB and/or phaB gene(s) is a *Ralstonia eutropha* gene, such as a *Ralstonia eutropha* H16 gene. In some embodiments, the pct gene is a *Megasphaera elsdenii* gene, such as a *Megasphaera elsdenii* BE2-2083 gene. In some embodiments, the tesB gene is an *Escherichia coli* gene, such as an *Escherichia coli* K12 gene.

Aspects of the invention relate to methods for producing 3,4-dihydroxybutyrate (3,4-DHBA), 2,3-dihydroxybutyrate (2,3-DHBA) and/or 3-hydroxybutyrolactone (3-HBL), comprising culturing a cell associated with the invention in minimal medium supplemented with a carbon source, to produce 3,4-dihydroxybutyrate (3,4-DHBA), 2,3-dihydroxybutyrate (2,3-DHBA) and/or 3-hydroxybutyrolactone (3-HBL). In some embodiments, the carbon source is glucose or glycerol. Methods can further comprise recovering the 3,4-DHBA, 2,3-DHBA and/or 3-HBL from the cell culture.

Aspects of the invention relate to a cell culture produced by culturing a cell associated with the invention. In some embodiments, the cell culture contains at least 0.1 g $L^{-1}$ 3,4-DHBA and/or 2,3-DHBA. In some embodiments, the cell culture contains at least 10 mg $L^{-1}$ 3-HBL.

Aspects of the invention relate to a supernatant of a cell culture produced by culturing a cell associated with the invention. In some embodiments, the supernatant is subjected to lactonization. In some embodiments, lactonization is achieved through acidification to reduce the pH of the supernatant, while in other embodiments, lactonization is achieved through auto-lactonization of DHBA-CoA.

Further aspects of the invention relate to methods for producing 3,4-dihydroxybutyrate (3,4-DHBA), 2,3-dihydroxybutyrate (DHBA) and/or 3-hydroxybutyrolactone (3-HBL) in a cell, including: increasing the expression of a ycdW gene, an aceA gene, and an aceK gene in the cell, relative to a wild type cell, through a first inducible expression system; expressing a pct gene, at least one of a phaA, thil, atoB or bktB gene, and at least one of a phaB or hbd gene in the cell, through a second inducible expression system; and culturing the cell in minimal medium supplemented with a carbon source.

In some embodiments, the cell further recombinantly expresses a tesB gene. In some embodiments, the cell has decreased or eliminated expression of an iclR gene, an aceB gene and a gcl gene, relative to a wild type cell The cell can be a bacterial cell, a fungal cell (including a yeast cell), a plant cell, an insect cell or an animal cell. In some embodiments, the cell is a bacterial cell, such as an *Escherichia coli* cell.

In some embodiments, the cell endogenously expresses ycdW, aceA, and/or aceK, and endogenous expression of ycdW, aceA, and/or aceK is increased through modification of the gene(s) and/or their promoter(s) and/or their ribosome binding sites (RBSs). In some embodiments, ycdW, aceA, and/or aceK are expressed from a plasmid. In some embodiments, one or more copies of ycdW, aceA, and/or aceK are integrated into the genome of the cell. In some embodiments, one or more of pct, phaA, thil, atoB, bktB, phaB or hbd is expressed from a plasmid. In some embodiments, one or more of pct, phaA, thil, atoB, bktB, phaB or hbd is integrated into the genome of the cell.

In some embodiments, the ycdW, aceA and/or aceK gene(s) is an *Escherichia coli* gene, such as an *Escherichia coli* K12 gene. In some embodiments, the phaA, bktB and/or phaB gene(s) is a *Ralstonia eutropha* gene, such as a *Ralstonia eutropha* H16 gene. In some embodiments, the pct gene is a *Megasphaera elsdenii* gene, such as a *Megasphaera elsdenii* BE2-2083 gene. In some embodiments, the tesB gene is an *Escherichia coli* gene, such as an *Escherichia coli* K12 gene.

In some embodiments, the carbon source is glucose or glycerol. In some embodiments, methods further comprise recovering 3,4-DHBA, 2,3-DHBA and/or 3-HBL from the cell culture. Further aspects of the invention relate to a cell culture produced by methods associated with the invention. In some embodiments, the cell culture contains at least 0.1 g L$^{-1}$ 3,4-DHBA and/or 2,3-DHBA. In some embodiments, the cell culture contains at least 10 mg L$^{-1}$ 3-HBL. Further aspects of the invention relate to a supernatant of a cell culture produced by a method associated with the invention. In some embodiments, the supernatant is subjected to lactonization. In some embodiments, lactonization is achieved through acidification to reduce the pH of the supernatant, while in other embodiments, lactonization is achieved through auto-lactonization of DHBA-CoA.

Further aspects of the invention relate to methods including: recombinantly expressing a pct gene, at least one of a phaA, thil, atoB or bktB gene, and at least one of a phaB or hbd gene in a cell that overexpresses a ycdW gene, an aceA gene, and an aceK gene.

These and other aspects of the invention, as well as various embodiments thereof, will become more apparent in reference to the drawings and detailed description of the invention. Each of the limitations of the invention can encompass various embodiments of the invention. It is, therefore, anticipated that each of the limitations of the invention involving any one element or combinations of elements can be included in each aspect of the invention.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
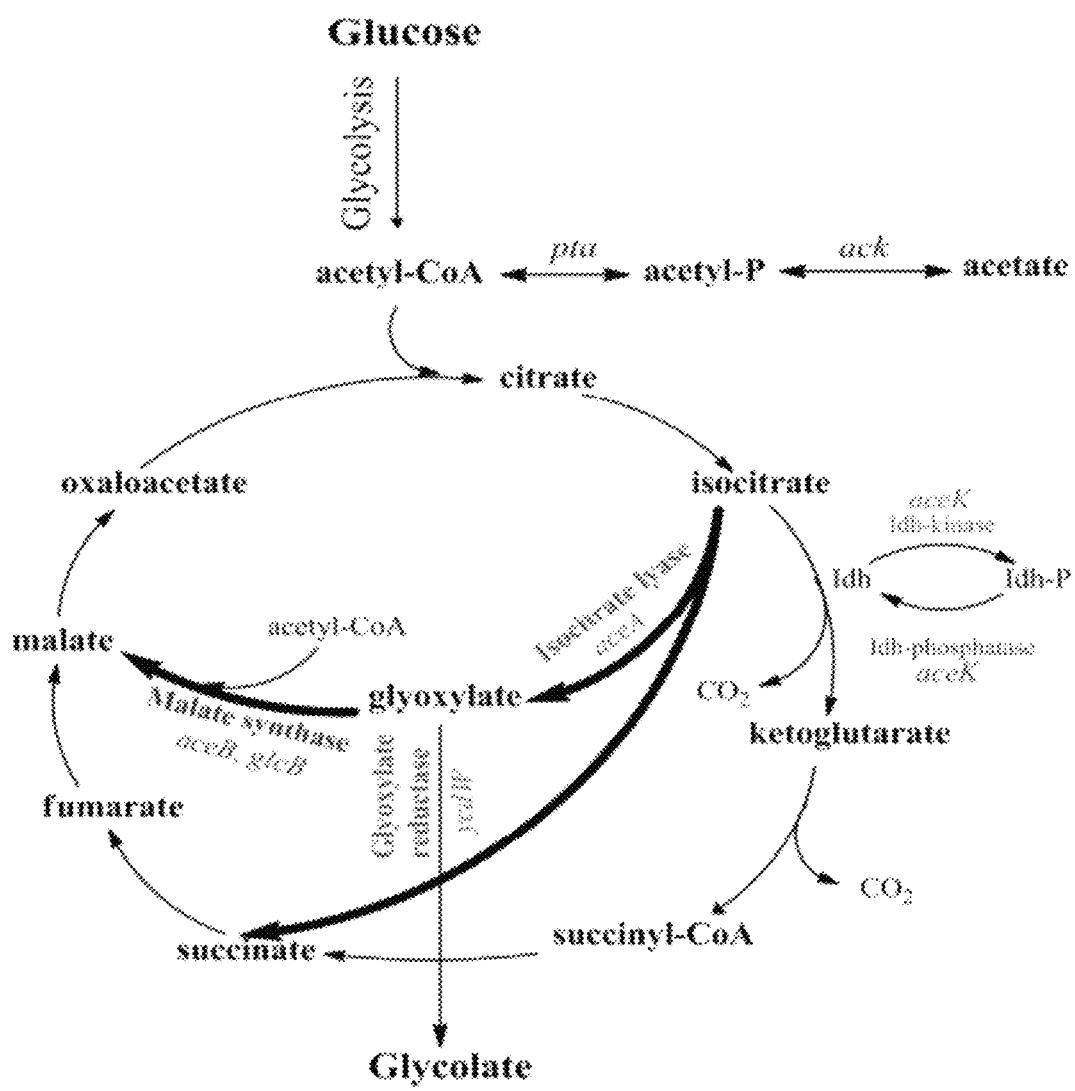
FIG. 1 presents a schematic depicting glycolate synthesis in *E. coli*. During growth on limited glucose or acetate, Idh-kinase/phosphatase phosphohorylates Idh, causing a drop in its activity, thereby reducing isocitrate flux through the TCA cycle. Simultaneous expression of isocitrate lyase (AceA) diverts isocitrate flux through the glyoxylate shunt, synthesizing glyoxylate which is reduced to glycolate by glyoxylate reductase (YcdW). The enzymes Idh-kinase (AceK), Isocitrate lyase (AceA) and Glyoxylate reductase (YcdW) promote glycolate synthesis while Idh-phosphatase (AceK) and Malate synthase (AceB, GlcB) are detrimental to glycolate synthesis.

Existing chemical synthesis routes for production of 3-HBL and DHBA employ harsh conditions, expensive materials and entail extensive post synthesis separations, making the synthesis of these valuable chiral building blocks economically unattractive. Described herein is the first demonstration of direct synthesis of DHBA and 3-HBL from a simple fermentable sugar as a sole feedstock. Cells associated with the invention are engineered to contain integrated pathways for glycolate synthesis and for 3,4-DHBA, 2,3-DHBA and 3-HBL synthesis, circumventing the need for glycolate to be supplied as an additional feedstock for cellular production of 3,4-DHBA, 2,3-DHBA and 3-HBL. Integration of these cellular pathways substantially improves the efficiency and cost-effectiveness of production of 3,4-DHBA, 2,3-DHBA and 3-HBL, allowing for their synthesis from simple and inexpensive sugar feedstocks, such as those derived from biomass.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional, items.

Methods described herein involve integration of two cellular pathways: a first pathway for production of glycolate, and a second pathway that uses glycolate for the synthesis of 3,4-DHBA, 2,3-DHBA and 3-HBL. Significantly, since both of these pathways are integrated within the same cell, the need for externally supplied glycolate is obviated, allowing for production of 3,4-DHBA, 2,3-DHBA and 3-HBL from simple fermentable sugars as a sole feedstock.

Glycolate Synthesis

Aspects of the invention relate to increasing glycolate production within a cell. As shown in FIG. 1, glycolate can be synthesized from glucose in a cell such as an *E. coli* cell. Increased production of glycolate from glucose in a cell can be achieved through manipulation of the endogenous glyoxylate shunt, as shown in FIG. 1. Enzymes such as Isocitrate dehydrogenase kinase/phosphatase (AceK), Isocitrate lyase (AceA) and Glyoxylate reductase (YcdW) promote glycolate synthesis, while enzymes such as Idh-phosphatase and Malate synthase (AceB, GlcB) are detrimental to glycolate synthesis.

The expression and/or activity of one or more of the enzymes involved in synthesizing glycolate from glucose can be altered for achieving increased production of glycolate. For example, expression and/or activity of one or more of AceK, AceA and YcdW can be increased to enhance glycolate synthesis. In some embodiments, aceK, aceA and/or ycdW are expressed endogenously in the cell while in other embodiments, aceK, aceA and/or ycdW are not expressed endogenously in the cell. Increased expression and/or activity of endogenous aceK, aceA and/or ycdW can be achieved by manipulation of one or more of the aceK, aceA and ycdW genes, their promoters and/or their ribosome binding sites. In some embodiments, all or part of the endogenous promoter of aceK, aceA and/or ycdW is replaced with an inducible promoter or a constitutively active promoter. Regardless of whether aceK, aceA and ycdW are expressed endogenously in the cell or not, one or more copies of aceK, aceA and/or ycdW can be expressed in the cell, either on one or more plasmids or through integration into the chromosome.

In some embodiments, ycdW, aceA and aceK are expressed together on an inducible plasmid such as pCOLA-Duet-ycdW-aceA-aceK, which is inducible using IPTG, or pHHD01K-ycdW-aceA-aceK, which is inducible using tetracycline or anhydro-tetracycline (aTc). As shown in the Examples, an *E. coli* K-12 strain transformed with pCOLA-Duet-ycdW-aceA-aceK or pHHD01K-ycdW-aceA-aceK synthesized up to approximately 1.5 g/L of glycolate, when cultured in minimal medium supplemented with glucose. As one of ordinary skill in the art would appreciate, many different types of inducible plasmids are compatible with aspects of the invention.

Figure 3:
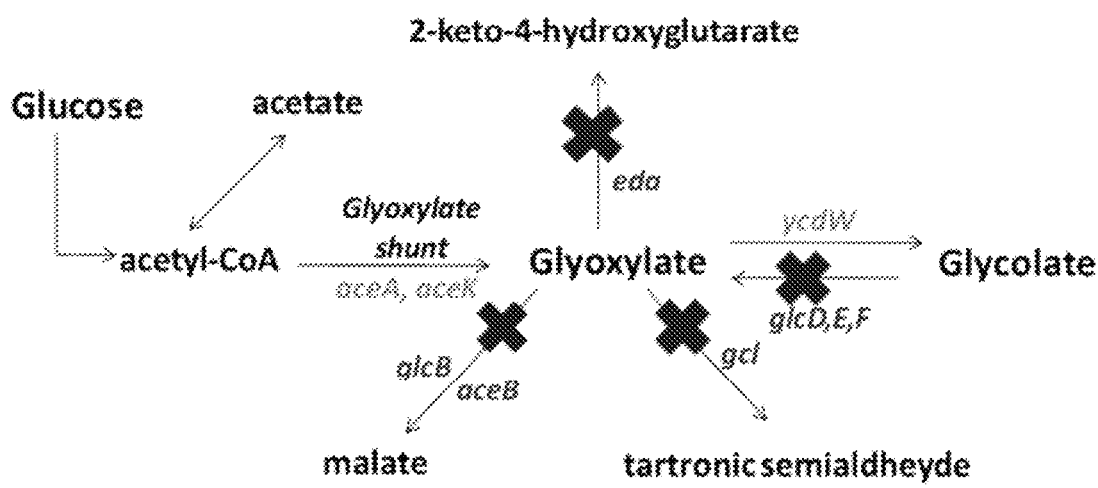
FIG. 3 presents a schematic depicting examples of gene knockouts for construction of an *E. coli* strain with attenuated glyoxylate and glycolate consumption.
Figure 4:
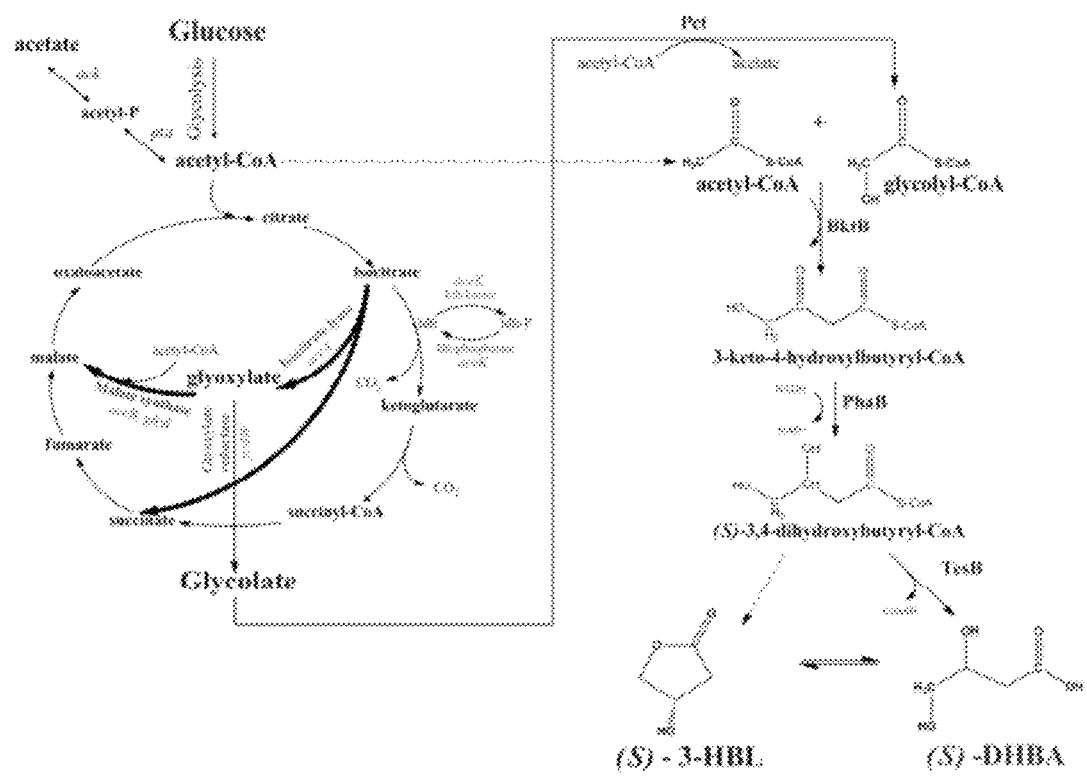
FIG. 4 presents a schematic depicting an integrated pathway for direct synthesis of 3,4-DHBA and 3-HBL using glucose as a single feedstock.

The expression and/or activity of one or more enzymes that are detrimental to production of glycolate from glucose can also be altered for achieving increased production of glycolate. In some embodiments, expression and/or activity of one or more of iclR, encoding a repressor of the aceBAK operon, gcl, encoding a Glyoxylate caroligase, and aceB, encoding a Malate synthase, is reduced or eliminated relative to the expression or activity of these genes in a wild type cell. It should be appreciated that the expression or activity of a gene such as iclR, gcl and/or aceB can be reduced or eliminated using any means known in the art. In some embodiments, iclR, gcl and aceB are each knocked out in the cell. In other embodiments, iclR, gcl and/or aceB can contain one or more mutations such as point mutations or deletions. In some embodiments, the expression or activity of one or more of glcD, glcE, glcF, aldA, eddA and eda is also reduced or eliminated in the cell relative to a wild type cell. FIG. 3 presents a schematic showing non-limiting examples of genes that can be knocked out in order attenuate glycolate consumption in a cell and increase glycolate production in the cell.

In some embodiments, a cell overexpresses one or more of ycdW, aceA and aceK and has reduced or eliminated expression of one or more of iclR, gcl and aceB, relative to a wild type cell. In certain embodiments, ycdW, aceA and aceK are each overexpressed and iclR, gcl and aceB are each knocked out in the cell.

Methods for attenuating glycolate consumption, and increasing glycolate production, in a cell, are disclosed in, and incorporated by reference from, US Patent Publication US 2009/0155867 (Soucaille). In US 2009/0155867, overexpression of YcdW was used to increase production of glycolate. However, nine different gene knockouts were required in order to achieve comparable glycolate titers to those that are demonstrated in the Examples of the instant application through overexpression of YcdW, AceA and AceK, combined with knockouts of only three genes: iclR, gcl and aceB. Without wishing to be bound by any theory, co-overexpression of YcdW, AceA and AceK may allow a cell to achieve high glycolate titers without having to knock out multiple genes. A strain with fewer gene knockouts is likely to be healthier than one with many gene knockouts, especially for growth on minimal medium, since it has many of the anaplerotic pathways intact, representing an advantage of the strains described herein over those described in US 2009/0155867.

It should also be appreciated that unlike in US 2009/0155867, where the goal of the engineered strains was to produce as much glycolate as possible from a cell, in methods described herein, glycolate production is integrated with pathways for production of 3,4-DHBA, 2,3-DHBA and 3-HBL, discussed further below. Thus, the goal was to construct strains capable of sustained glycolate synthesis, rather than maximum glycolate synthesis. Optimization of glycolate production can involve an assessment of levels of production of 3,4-DHBA, 2,3-DHBA and 3-HBL. In some embodiments, an optimal level of glycolate production is that level which permits optimal production of 3,4-DHBA, 2,3-DHBA and/or 3-HBL.

Since acetyl-CoA is a common intermediate for both glycolate and DHBA synthesis, its distribution along the two pathways can be optimized. A strain engineered for maximum glycolate synthesis (such as those described in US 2009/0155867) may not be optimal for 3,4-DHBA, 2,3-DHBA and 3-HBL synthesis. Too many knocked out genes can result in excessive diversion of acetyl-CoA towards glycolate synthesis, leaving little for 3,4-DHBA, 2,3-DHBA or 3-HBL synthesis. Additionally, too many gene knockouts can also result in an unhealthy cell which may not be capable of expressing the recombinant genes discussed below for synthesis of 3,4-DHBA, 2,3-DHBA and 3-HBL.

While cells associated with the invention can be grown in a range of different media conditions, including minimal and rich media, growth in minimal medium is beneficial for functioning of the glyoxylate shunt. However, as demonstrated in the Examples, co-expression of all of different enzymes for glycolate synthesis and synthesis of 3,4-DHBA, 2,3-DHBA and 3-HBL during growth in minimal medium imposes considerable metabolic burden on cells, which can hamper effective expression of one or more enzymes. Thus, simple cloning of each gene into a plasmid and attempting to express them in the strains discussed in US 2009/0155867 would not have achieved direct synthesis of DHBA or 3-HBL from glucose. As demonstrated in the Examples, after extensive efforts to overcome the effects of metabolic burden in cells, one effective strategy that was uncovered for dealing with metabolic burden was to distribute the different pathway enzymes between two or more different inducible expression systems. Unexpectedly, this distributed expression substantially increased production of DHBA and 3-HBL. As used herein, distributed expression refers to expressing two or more genes in a cell using two or more different inducible expression systems. In some embodiments, if a gene is endogenously expressed, its expression can be induced by replacing its promoter with an inducible or constitutively active promoter.

Direct Synthesis of DHBA and 3-HBL

A biosynthetic pathway for production of 3-hydroxyacids such as DHBA and 3-HBL was demonstrated in, and is incorporated by reference from, WO/2010/101651 (Martin et al.). In the biosynthetic pathway described in WO/2010/101651, also referred to herein as "the 3-hydroxyalkanoic acid pathway," glycolate was added to the cells as a feedstock in the medium for synthesis of DHBA and 3-HBL.

By contrast, cells described herein are genetically engineered to produce glycolate, which can feed into the DHBA and 3-HBL synthesis pathway, obviating the need to supply glycolate as an additional feedstock. This integrated approach significantly improves the efficiency and cost-effectiveness of the biosynthetic production of these valuable chiral building blocks.

The 3-Hydroxyalkanoic Acid Pathway

Methods and compositions described herein use the 3-hydroxyalkanoic acid pathway to synthesize 3-hydroxyacids such as 3-hydroxybutyrolactone (3-HBL) and/or its hydrolyzed form 3,4-dihydroxybutyric acid (3,4-DHBA) and 2,3-dihydroxybutyric acid (2,3-DHBA) from sugars and sugar-derived substrates. As used herein, a "hydroxyacid" refers to a compound that contains both a carboxyl and a hydroxyl moiety. As used herein "DHBA" refers to 3,4-dihydroxybutyric acid (3,4-DHBA) and/or 2,3-dihydroxybutyric acid (2,3-DHBA).

Figure 2:
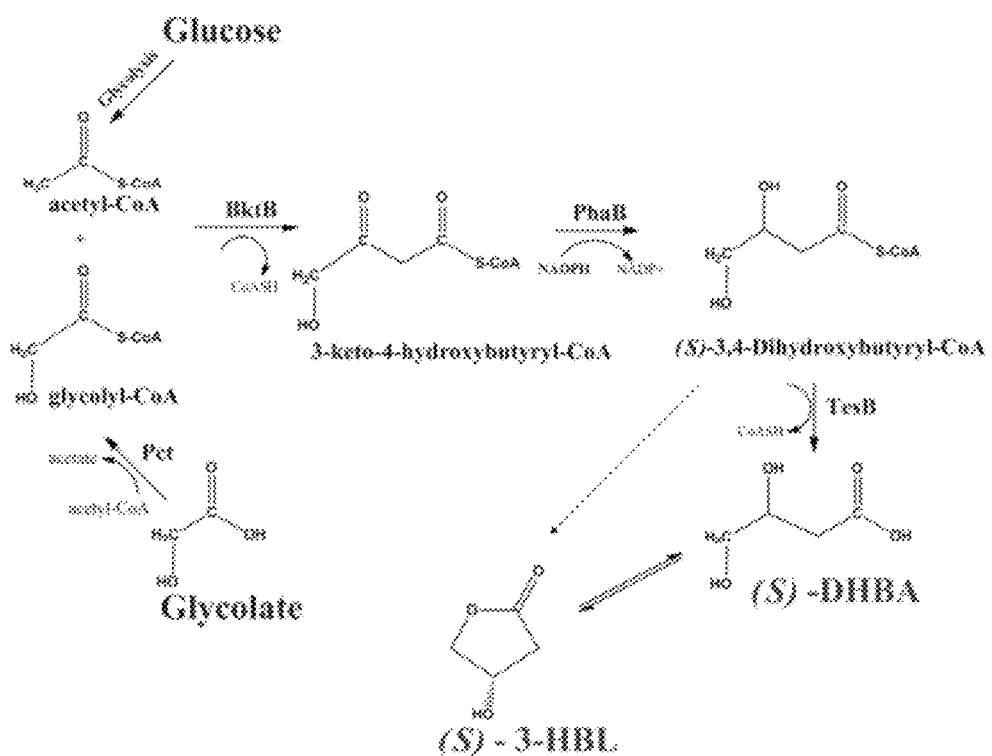
FIG. 2 presents a schematic depicting a pathway for 3,4-DHBA and 3-HBL production from glucose and glycolate. Expression of Pct, BktB, PhaB and TesB in *E. coli* allows 3,4-DHBA and 3-HBL synthesis. Pct activates glycolate to glycoly-CoA. BktB brings about condensation with acetyl-CoA (from glycolysis) to form 4-hydroxy-3-ketobutyryl-CoA, which is reduced by PhaB to 3,4-dihydroxybutyryl-CoA. TesB cleaves 3,4-dihydroxybutyryl-CoA to form 3,4-DHBA, while a part of the 3,4-dihydroxybutyryl-CoA spontaneously lactonizes to 3-HBL.

FIG. 2 presents a schematic of the 3-hydroxyalkanoic acid pathway. In methods and compositions associated with the invention, one or more acetoacetyl-CoA thiolases (such as thil, bktB, phaA or atoB) is used to perform a condensation reaction to yield a 3-ketoacyl-CoA intermediate, which is subsequently reduced by either phaB or hbd to yield a 3-hydroxyacyl-CoA compound. Optionally, the CoA moiety from the 3-hydroxyacyl-CoA compound can be hydrolyzed by tesB, liberating the free 3-hydroxyacid.

Short chain acyl-CoA compounds that would be candidate substrates for this pathway are not readily available metabolites in *E. coli*. To circumvent this, propionyl-CoA transferase (pct), an enzyme with broad substrate-specificity, is used to exchange CoA moieties between short-chain organic acids. In methods and compositions described herein, pct is used to transfer CoA from acetyl-CoA to a substrate such as an acid supplied to the cell, forming the acyl-CoA for use by the pathway. In some embodiments, a phosphotransbutyrase (ptb) gene and a butyrokinase (buk) gene are used to produce propionyl-CoA instead of pct.

Aspects of the invention relate to recombinant expression of one or more genes encoding for one or more enzymes in the 3-hydroxyalkanoic acid pathway. Enzymes associated with this pathway include thiolases (encoded by thil, bktB, phaA or atoB) and reductases (phaB, hbd or Sl). Aspects of the invention also relate to recombinant expression of propionyl-CoA transferase (encoded by pct) and thioesterase B (encoded by tesB).

Aspects of the invention relate to cell(s) that recombinantly express one or more genes associated with the invention, and the use of such cells in producing glycolate, 3,4-DHBA, 2,3-DHBA and 3-HBL. In some embodiments, the cell is cultured in minimal medium supplemented with glucose or glycerol as the only carbon and energy source during which time glycolate, 3,4-DHBA, 2,3-DHBA and 3-HBL are produced and excreted into the culture medium. 3-HB is also synthesized as a by-product. Growth in minimal medium ensures appreciable flux through the glyoxylate shunt (which is heavily repressed during growth in rich medium) for effective glycolate synthesis. Further, acetyl-CoA is a common metabolic intermediate in both. In minimal medium, the accumulation of acetate formed from acetyl-CoA due to excess glycolytic flux stimulates flux through the glyoxylate shunt. High acetyl-CoA levels maintain a high flux through the glyoxylate shunt for glycolate synthesis, ensuring efficient activation of glycolate to glycolyl-CoA (since Pct transfers CoA from acetyl-CoA to glycolate in the activation step in the DHBA and 3-HBL pathway) and condensation of glycolyl-CoA with acetyl-CoA by BktB. High acetyl-CoA levels can also result in loss of carbon in the form of by-products such as acetate and 3-HB. Thus, as discussed further herein, in the integrated pathway, one of the mechanisms for optimizing the intracellular acetyl-CoA levels is to vary the feed glucose concentration to achieve selective DHBA and 3-HBL synthesis.

Further aspects of the invention relate to methods for producing 2,3-DHBA in the presence of glycolate using cells that may or may not be engineered to modulate glycolate synthesis. For example, methods include use of cells that recombinantly express a pct gene, at least one of a phaA, thil, atoB or bktB gene, and at least one of a phaB or hbd gene, for the production of 2,3-DHBA.

Using the integrated pathway described herein, titers of up to 1.36 g/L for DHBA and 0.13 g/L for 3-HBL in the *E. coli* strain MG1655 (DE3) ΔiclR, Δgcl, ΔaceB, expressing the glycolate pathway genes (ycdW, aceA and aceK) and DHBA and 3-HBL pathway genes (bktB, phaB, pct and tesB), grown in minimal medium supplemented with 1.5 wt/vol % glucose at the shake flask scale after 90 hours of fermentation at 30° C. As discussed further herein, expression of pathway enzymes was distributed between two separately inducible expression systems.

It should be appreciated that the genes associated with the invention can be obtained from a variety of sources. In some embodiments, the phaA, phaB, and bktB genes are obtained from a strain of *Ralstonia eutropha*, such as *Ralstonia eutropha* H16, the tesB gene is obtained from a strain of *Escherichia coli* such as *Escherichia coli* K12, the pct gene is obtained from a strain of *Megasphaera elsdenii*, such as *Megasphaera elsdenii* BE2-2083, the atoB gene is obtained from a strain of *P. putida*, such as *P. putida* KT2440, the hbd and thil genes are obtained from a strain of *Clostridium acetobutylicum*, such as *C. acetobutylicum* 824, and the SI gene is obtained from a strain of *C. magnolia*. In some embodiments, the ycdW, aceA and aceK genes are *Escherichia coli* genes, such as *Escherichia coli* K 12 genes. In some embodiments, wherein ptb and buk are expressed instead of pct, the ptb and buk genes are coexpressed on an operon. In some embodiments, the ptb-buk operon is obtained from a strain of *Clostridium acetobutylicum*.

In some embodiments, the sequence of the phaA gene is represented by GenBank accession no. P14611 (Peoples and Sinskey, 1989), the sequence of the phaB gene is represented by GenBank accession no. P14697 (Peoples and Sinskey, 1989), the sequence of the tesB gene is represented by Genbank accession no. P23911 or ABC97996 (Naggert et al., 1991) and the sequence of the pct gene is represented by the sequence depicted in (Taguchi et al., 2008; incorporated by reference from SEQ ID NO:9 in WO/2010/101651). In some embodiments, the sequence of the ptb gene is represented by Genbank accession no. AAK81016. In some embodiments, the sequence of the buk gene is represented by Genbank accession no. AAK81015. In some embodiments, the sequence of the ycdW gene is represented by UniProt accession no. P75913 or GenBank accession no. NP_415551.2. In some embodiments, the sequence of the aceA gene is represented by UniProt accession no. P0A9G6 or GenBank accession no. AP_004516.1. In some embodiments, the sequence of the aceK gene is represented by UniProt accession no. P11071 or GenBank accession no. AP_004517. It should be appreciated that any of the nucleic acids and/or polypeptides described herein can be codon-optimized and expressed recombinantly in a codon-optimized form.

As one of ordinary skill in the art would be aware, homologous genes for these enzymes could be obtained from other species and could be identified by homology searches, for example through a protein BLAST search, available at the National Center for Biotechnology Information (NCBI) internet site (ncbi.nlm.nih.gov). Genes associated with the invention can be PCR amplified from DNA from any source of DNA which contains the given gene. In some embodiments, genes associated with the invention are synthetic. Any means of obtaining a gene encoding the enzymes associated with the invention are compatible with the instant invention.

The invention thus involves recombinant expression of genes encoding enzymes discussed above, functional modifications and variants of the foregoing, as well as uses relating thereto. Homologs and alleles of the nucleic acids associated with the invention can be identified by conventional techniques. Also encompassed by the invention are nucleic acids that hybridize under stringent conditions to the nucleic acids described herein. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/ 0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5×SSC/0.1×SDS at temperatures up to 68° C.

There are other conditions, reagents, and so forth which can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of nucleic acids of the invention (e.g., by using lower stringency conditions). The skilled artisan also is familiar with the methodology for screening cells and libraries for expression of such molecules which then are routinely isolated, followed by isolation of the pertinent nucleic acid molecule and sequencing.

In general, homologs and alleles typically will share at least 75% nucleotide identity and/or at least 80% amino acid identity to the sequences of nucleic acids and polypeptides, respectively, in some instances will share at least 90% nucleotide identity and/or at least 90 or 95% amino acid identity and in still other instances will share at least 95% nucleotide identity and/or at least 99% amino acid identity. In some embodiments, homologs and alleles will share at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% nucleotide identity to the sequences of nucleic acids and/or 80%, 81%, 82%, 83%, 84%, 85%, 86%, 87%, 88%, 89%, 90%, 91%, 92%, 93%, 94%, 95%, 96%, 97%, 98%, or 99% identity to the sequences of polypeptides.

The homology can be calculated using various, publicly available software tools developed by NCBI (Bethesda, Md.) that can be obtained through the NCBI internet site. Exemplary tools include the BLAST software, also available at the NCBI internet site (www.ncbi.nlm.nih.gov). Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code. The invention also embraces codon optimization to suit optimal codon usage of a host cell.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as enzymatic activity. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art.

For example, modified nucleic acid molecules which encode polypeptides having single amino acid changes can be prepared. Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2-6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

The invention embraces variants of polypeptides. As used herein, a "variant" of a polypeptide is a polypeptide which contains one or more modifications to the primary amino acid sequence of the polypeptide. Modifications which create a variant can be made to a polypeptide 1) to reduce or eliminate an activity of a polypeptide; 2) to enhance a property of a polypeptide; 3) to provide a novel activity or property to a polypeptide, such as addition of an antigenic epitope or addition of a detectable moiety; or 4) to provide equivalent or better binding between molecules (e.g., an enzymatic substrate). Modifications to a polypeptide are typically made to the nucleic acid which encodes the polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the amino acid sequence. One of skill in the art will be familiar with methods for predicting the effect on protein conformation of a change in protein sequence, and can thus "design" a variant of a polypeptide according to known methods. One example of such a method is described by Dahiyat and Mayo in *Science* 278:82-87, 1997, whereby proteins can be designed de novo. The method can be applied to a known protein to vary a only a portion of the polypeptide sequence. By applying the computational methods of Dahiyat and Mayo, specific variants of a polypeptide can be proposed and tested to determine whether the variant retains a desired conformation.

In general, variants include polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present).

Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a gene or cDNA clone to enhance expression of the polypeptide. The activity of variant polypeptides can be tested by cloning the gene encoding the variant polypeptide into a bacterial or mammalian expression vector, introducing the vector into an appropriate host cell, expressing the variant polypeptide, and testing for a functional capability of the polypeptides as disclosed herein.

The skilled artisan will also realize that conservative amino acid substitutions may be made in polypeptides to provide functionally equivalent variants of the foregoing polypeptides, i.e., the variants retain the functional capabilities of the polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of polypeptides include conservative amino acid substitutions in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In general, it is preferred that fewer than all of the amino acids are changed when preparing variant polypeptides. Where particular amino acid residues are known to confer function, such amino acids will not be replaced, or alternatively, will be replaced by conservative amino acid substitutions. Preferably, 1, 2, 3, 4, 5, 6, 7, 8, 9, 10, 11, 12, 13, 14, 15, 16, 17, 18, 19, 20 residues can be changed when preparing variant polypeptides. It is generally preferred that the fewest number of substitutions is made. Thus, one method for generating variant polypeptides is to substitute all other amino acids for a particular single amino acid, then assay activity of the variant, then repeat the process with one or more of the polypeptides having the best activity.

Conservative amino-acid substitutions in the amino acid sequence of a polypeptide to produce functionally equivalent variants of the polypeptide typically are made by alteration of a nucleic acid encoding the polypeptide. Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding a polypeptide.

The invention encompasses any type of cell that recombinantly expresses genes associated with the invention, including prokaryotic and eukaryotic cells. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp. The bacterial cell can be a Gram-negative cell such as an *Escherichia coli* (*E. coli*) cell, or a Gram-positive cell such as a species of *Bacillus*. In other embodiments the cell is a fungal cell such as yeast cells, e.g., *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp, and industrial polyploid yeast strains.

Preferably the yeast strain is a *S. cerevisiae* strain. Other examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp. In other embodiments the cell is an algal cell, a plant cell, or a mammalian cell. It should be appreciated that some cells compatible with the invention may express an endogenous copy of one or more of the genes associated with the invention as well as a recombinant copy. In some embodiments if a cell has an endogenous copy of one or more of the genes associated with the invention then the methods will not necessarily require adding a recombinant copy of the gene(s) that are endogenously expressed. In some embodiments the cell may endogenously express one or more enzymes from the pathways described herein and may recombinantly express one or more other enzymes from the pathways described herein for efficient production of 3,4-DHBA, 2,3-DHBA and/or 3-HBL.

In some embodiments, one or more of the genes associated with the invention is expressed in a recombinant expression vector. As used herein, a "vector" may be any of a number of nucleic acids into which a desired sequence or sequences may be inserted by restriction and ligation for transport between different genetic environments or for expression in a host cell. Vectors are typically composed of DNA although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell such as a host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

When the nucleic acid molecule that encodes any of the enzymes of the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell. Heterologous expression of genes associated with the invention, for production of 3,4-DHBA, 2,3-DHBA and 3-HBL, is demonstrated in the Examples section using *E. coli*. The novel method for producing 3,4-DHBA, 2,3-DHBA and 3-HBL can also be expressed in other bacterial cells, archaeal cells, fungi (including yeast cells), mammalian cells, plant cells, etc.

A nucleic acid molecule that encodes the enzyme of the claimed invention can be introduced into a cell or cells using methods and techniques that are standard in the art. For example, nucleic acid molecules can be introduced by standard protocols such as transformation including chemical transformation and electroporation, transduction, particle bombardment, etc. Expressing the nucleic acid molecule encoding the enzymes of the claimed invention also may be accomplished by integrating the nucleic acid molecule into the genome.

In some embodiments one or more genes associated with the invention is expressed recombinantly in a bacterial cell. Bacterial cells according to the invention can be cultured in media of any type (rich or minimal) and any composition. In some embodiments, the cells are culture in minimal medium. As would be understood by one of ordinary skill in the art, routine optimization would allow for use of a variety of types of media. The selected medium can be supplemented with various additional components. Some non-limiting examples of supplemental components include glucose, antibiotics, IPTG, tetracycline or anhydro-tetracycline (aTc) for gene induction and ATCC Trace Mineral Supplement. Similarly, other aspects of the medium, and growth conditions of the cells of the invention may be optimized through routine experimentation. For example, pH and temperature are non-limiting examples of factors which can be optimized. In some embodiments, factors such as choice of media, media supplements, and temperature can influence production levels of 3-hydroxyacids such as 3,4-DHBA, 2,3-DHBA and/or 3-HBL. In some embodiments the concentration and amount of a supplemental component may be optimized. In some embodiments, how often the media is supplemented with one or more supplemental components, and the amount of time that the media is cultured before harvesting 3,4-DHBA, 2,3-DHBA and/or 3-HBL is optimized.

Cells associated with the invention are provided with fermentable sugars as feedstocks. In some embodiments, the cell is provided with one fermentable sugar as a sole feedstock. In some embodiments, the fermentable sugar is glucose or glycerol. It should be appreciated that other fermentable sugars are also compatible with methods described herein. In some embodiments, the fermentable sugar is derived from biomass.

Figure 5:
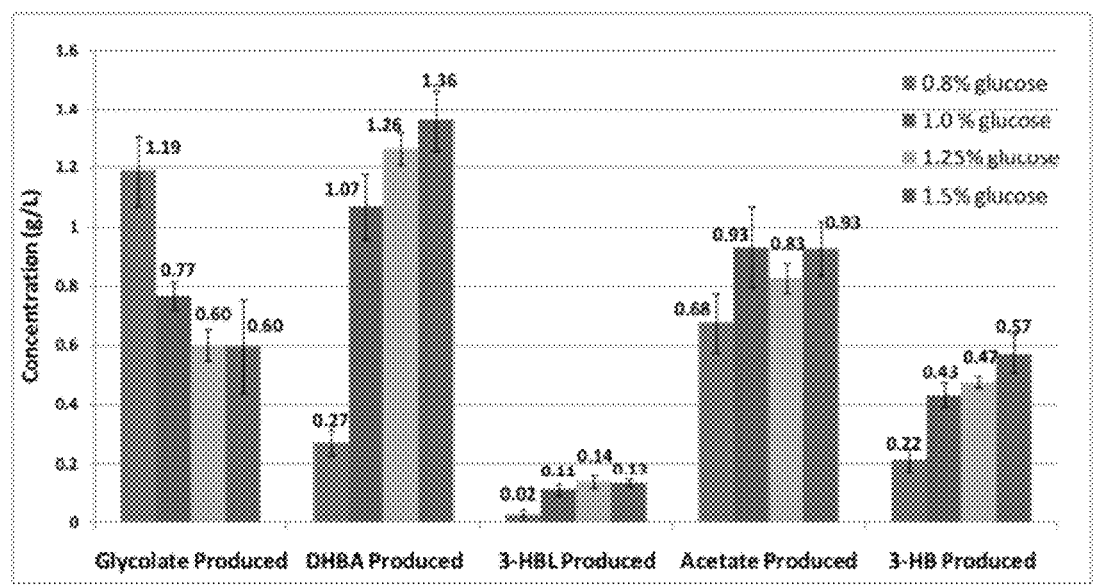
FIG. 5 presents a graph demonstrating titers of various product accumulation. MG1655 (DE3) ΔiclR, ΔaceB, Δgcl expressing the glycolate pathway genes (ycdW, aceA and aceK) off pHHD01-ycdW-aceA-aceK and DHBA and 3-HBL pathway genes (bktB, phaB, pct, tesB) off pETDuet-bktB-phaB and pCDFDuet-pct-tesB, were grown in minimal medium in shake flask fermentations supplemented with varying amounts of glucose after 90 hours at 30° C. The various acid products were analyzed (identified and quantified) by HPLC on an Aminex® HPX-87H column using 5 mM sulfuric acid as the mobile phase.
Figure 6:
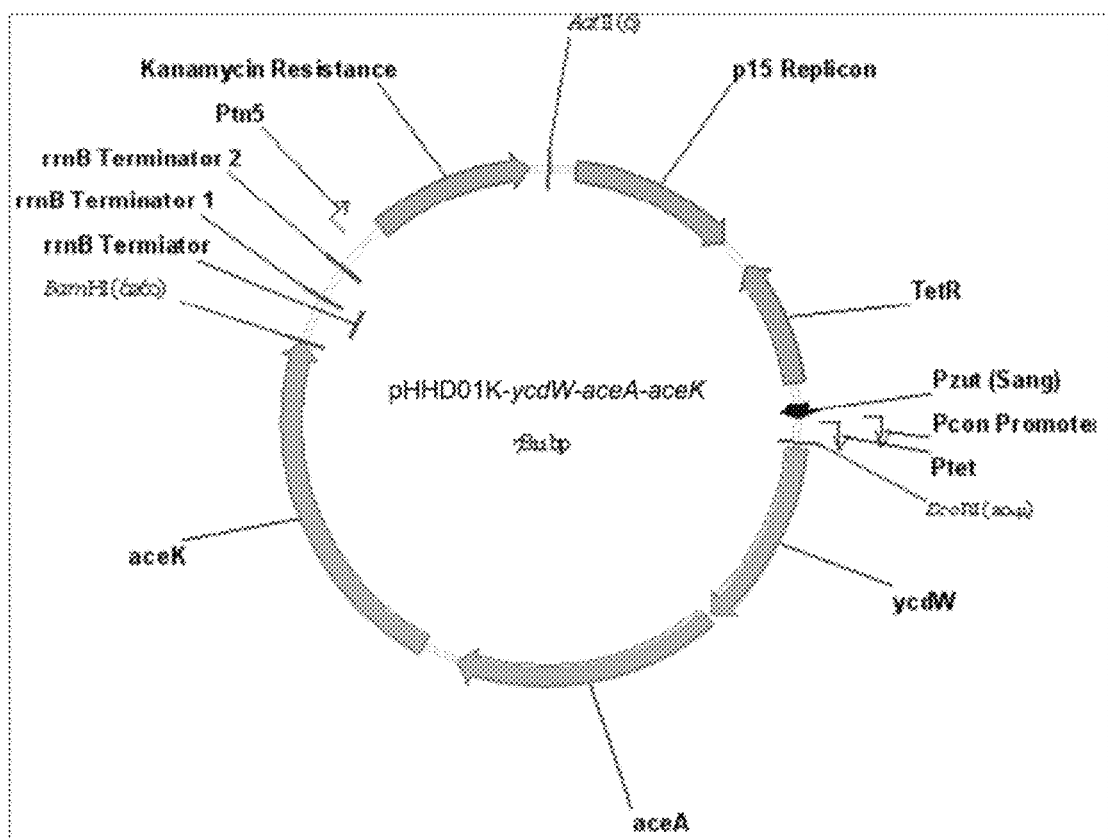
FIG. 6 depicts the aTc inducible plasmid: pHHD01-ycdW-aceA-aceK. This expression plasmid, containing an operon of glycolate pathway enzymes (ycdW-aceA-aceK), was constructed using SOEing PCR by amplifying the aceBAK operon and swapping the aceB gene for ycdW. The resulting operon was cloned into an expression vector carrying the aTc inducible Tet promoter.

In some embodiments, the concentration of the fermentable sugar, such as glucose or glycerol, that is supplied to the culture medium is optimized. In certain embodiments, the concentration of the fermentable sugar is approximately 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9% or more than 3.9%. FIG. 5 shows the variation of the DHBA, glycolate and 3-HBL titers in addition to acetate and 3-HB titers for various feed glucose concentrations for the same strain, cultured in minimal medium supplemented with various feed concentrations of glucose at 30° C. The yields on glucose in terms of total moles of DHBA and 3-HBL synthesized per mole of glucose supplied for various feed glucose concentrations in the same experiment are shown in Table 2. The total molar yields of the various products are observed to vary with the feed glucose concentrations, with, in some embodiments, the highest value of total molar yield for DHBA and 3-HBL over glucose observed for a feed glucose concentration of 1 wt./vol % or 10 g/L.

In some embodiments the concentration of an inducer molecule is optimized. In certain embodiments, the inducer is IPTG and the concentration of IPTG is approximately 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, 250 μm, 260 μm, 270 μm, 280 μm, 290 μm, 300 μm, 310 μm, 320 μm, 330 μm, 340 μm, 350 μm, 360 μm, 370 μm, 380 μm, 390 μm, 400 μm, 410 μm, 420 μm, 430 μm, 440 μm, 450 μm, 460 μm, 470 μm, 480 μm, 490 μm, 500 μm, 525 μm, 550 μm, 575 μm, 600 μm, 625 μm, 650 μm, 675 μm, 700 μm, 725 μm, 750 μm, 775 μm, 800 μm, 825 μm, 850 μm, 875 μm, 900 μm, 925 μm, 950 μm, 975 μm, 1000 μm, 1025 μm, 1050 μm, 1100 μm or is more than 1100 μm.

In some embodiments, the inducer is tetracycline or anhydro-tetracycline (aTc) and the concentration of tetracycline or anhydro-tetracycline (aTc) is approximately 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, 200 ng/ml, 210 ng/ml, 220 ng/ml, 230 ng/ml, 240 ng/ml, 250 ng/ml, 260 ng/ml, 270 ng/ml, 280 ng/ml, 290 ng/ml, 300 ng/ml, 310 ng/ml, 320 ng/ml, 330 ng/ml, 340 ng/ml, 350 ng/ml, 360 ng/ml, 370 ng/ml, 380 ng/ml, 390 ng/ml, 400 ng/ml, 410 ng/ml, 420 ng/ml, 430 ng/ml, 440 ng/ml, 450 ng/ml, 460 ng/ml, 470 ng/ml, 480 ng/ml, 490 ng/ml, 500 ng/ml, 510 ng/ml, 520 ng/ml, 530 ng/ml, 540 ng/ml, 550 ng/ml, 560 ng/ml, 570 ng/ml, 580 ng/ml, 590 ng/ml, 600 ng/ml, 610 ng/ml, 620 ng/ml, 630 ng/ml, 640 ng/ml, 650 ng/ml, 660 ng/ml, 670 ng/ml, 680 ng/ml, 690 ng/ml, 700 ng/ml, 725 ng/ml, 750 ng/ml, 775 ng/ml, 800 ng/ml, 825 ng/ml, 850 ng/ml, 875 ng/ml, 900 ng/ml, 925 ng/ml, 950 ng/ml, 975 ng/ml, 1000 ng/ml or more than 1000 ng/ml. It should be appreciated that other inducer molecules are also compatible with methods described here and that optimization of the concentrations of such inducer molecules can be achieved through routine experimentation.

According to aspects of the invention, high titers of DHBA and/or 3-HBL are produced through the recombinant expression of genes associated with the invention, in a cell. As used herein "high titer" refers to a titer in the milligrams per liter (mg $L^{-1}$) scale. The titer produced for a given product will be influenced by multiple factors including choice of media.

In some embodiments the titer of DHBA is at least 25 mg $L^{-1}$. For example the titer may be at least approximately 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 400, 425, 450, 475, 500, 525, 550, 575, 600, 625, 650, 675, 700, 750, 775, 800 or 900 mg $L^{-1}$, or 1, 1.1, 1.2, 1.3, 1.4, 1.5, 1.6, 1.7, 1.8. 1.9, 2, 2.1, 2.2, 2.3, 2.4, 2.5, 2.6, 2.7, 2.8, 2.9, 3, 3.5, 4, 4.5, 5, or more than 5 g $L^{-1}$.

In some embodiments the titer for production of 3-HBL is at least 1 mg $L^{-1}$. For example the titer may be at least approximately 1, 2, 3, 4, 5, 6, 7, 8, 9, 10, 15, 20, 25, 30, 35, 40, 45, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850 or 900 mg $L^{-1}$, or 1, 1.5, 2, 2.5, 3, 3.5, 4, 4.5, 5 or more than 5 g $L^{-1}$.

In some embodiments, cells and methods associated with the invention can be used for production of glycolate. In some embodiments the titer for production of 3-HBL is at least 50 mg $L^{-1}$. For example, the titer may be at least approximately 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 400, 425, 450, 475, 500, 525, 550, 575, 600, 625, 650, 675, 700, 750, 775, 800 or 900 mg $L^{-1}$, or 1, 1.5, 2, 2.5, 3, 3.5, 4, 4.5, 5, or more than 5 g $L^{-1}$.

As demonstrated in the Examples, the use of more than one independent inducible expression system to express the collection of enzymes associated with the two integrated pathways, led to surprisingly efficient production of DHBA and 3-HBL from intracellular glycolate. As shown in Example 10, MG1655 (DE3) ΔiclR, Δgcl, ΔaceB cells transformed with glycolate pathway plasmid, pHHD01K-ycdW-aceA-aceK in minimal medium supplemented with 0.8% glucose at 30° C. with varying concentrations of aTc resulted in titers of about 1.5 g/L for induction levels of 250 ng/ml to 500 ng/ml. Moreover, MG1655 (DE3) ΔiclR, Δgcl, ΔaceB cells transformed with pHHD01K-ycdW-aceA-aceK, and DHBA pathway plasmids (pETDuet-bktB-phaB and pCDFDuet-pct-tesB), cultured in minimal medium supplemented with 0.8% glucose, on induction with 100 ng/ml, 250 ng/ml and 500 ng/ml aTc and 1 mM IPTG, made up to 1 g/L of glycolate even in the presence of the DHBA plasmids.

The 3-hydroxyalkanoic pathway can be modulated to produce more DHBA or 3-HBL through the presence or absence of the thioesterase TesB. In some embodiments, recombinant expression of tesB leads to production of significantly more DHBA than 3-HBL. In some embodiments, without tesB expression, more 3-HBL is made than DHBA. Without wishing to be bound by any theory, the small amount of DHBA formed in the absence of recombinant tesB may be due to the expression of genomic tesB, as this gene is native to *E. coli* (Huisman et al., 1991).

Lactonization can be used to improve titers of 3-HBL. As used herein, lactonization refers to formation of a lactone by intramolecular attack of a hydroxyl group on an activated carbonyl group. Supernatants from cultures that produce more DHBA than 3-HBL can be acidified, such as through addition of hydrochloric acid, to reduce the pH. Incubation of these supernatants, for example at 37° C. overnight, allows for acid-catalyzed lactonization, resulting in improved titers of 3-HBL. The observation that in the absence of tesB, more 3-HBL is produced while little DHBA is made, suggests that DHBA-CoA can self-lactonize into 3-HBL in vivo.

In some embodiments, acid post-treatment of culture supernatants increases 3-HBL titer by greater than 10%. In other embodiments, acid post-treatment of culture supernatants increases 3-HBL titer by greater than 100%. For example, 3-HBL titers can be increased by approximately 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250% or more than 250% including any intermediate values. In some embodiments, acid post-treatment of culture supernatants leads to a reduction in titer of DHBA of greater than 10%. For example, titer of DHBA can be reduced by approximately 10%, 20%, 30%, 40%, 50%, 60%, 70%, 80%, 85%, 90%, 95% or more than 95% including any intermediate values.

The liquid cultures used to grow cells associated with the invention can be housed in any of the culture vessels known and used in the art. In some embodiments, large scale production in an aerated reaction vessel such as a stirred tank reactor can be used to produce large quantities of 3,4-DHBA, 2,3-DHBA and/or 3-HBL.

Aspects of the invention include strategies to optimize production of 3,4-DHBA, 2,3-DHBA and/or 3-HBL from a cell. Optimized production of 3,4-DHBA, 2,3-DHBA and/or 3-HBL refers to producing a higher amount of a 3,4-DHBA, 2,3-DHBA and/or 3-HBL following pursuit of an optimization strategy than would be achieved in the absence of such a strategy. One strategy for optimization is to increase expression levels of one or more genes associated with the invention through selection of appropriate promoters and ribosome binding sites. In some embodiments this may include the selection of high-copy number plasmids, or low or medium-copy number plasmids. In some embodiments the plasmid is a medium-copy number plasmid such as pETDuet. The step of transcription termination can also be targeted for regulation of gene expression, through the introduction or elimination of structures such as stem-loops.

In some embodiments it may be advantageous to use a cell that has been optimized for production of 3,4-DHBA, 2,3-DHBA and/or 3-HBL. In some embodiments, screening for mutations that lead to enhanced production of 3,4-DHBA, 2,3-DHBA and/or 3-HBL may be conducted through a random mutagenesis screen, or through screening of known mutations. In some embodiments shotgun cloning of genomic fragments could be used to identify genomic regions that lead to an increase in production of 3,4-DHBA, 2,3-DHBA and/or 3-HBL, through screening cells or organisms that have these fragments for increased production of 3,4-DHBA, 2,3-DHBA and/or 3-HBL. In some cases one or more mutations may be combined in the same cell or organism.

Optimization of production of 3,4-DHBA, 2,3-DHBA and/or 3-HBL can involve optimizing selection of bacterial strains for expression of recombinant pathways described herein. In some embodiments, use of a bacterial strain that is close to wild-type, meaning a strain that has not been substantially genetically modified, may lead to increased titers of 3,4-DHBA, 2,3-DHBA and/or 3-HBL. For example, in some embodiments, use of a bacterial strain which expresses recA and/or endA genes, such as E. coli strain MG1655(DE3) leads to increased titers of 3,4-DHBA, 2,3-DHBA and/or 3-HBL. Stereochemistry of molecules produced through the recombinant pathways described herein can be controlled by the choice of 3-hydroxybutyryl-CoA reductase. In certain embodiments, the use of PhaB results in (R)-3-hydroxyacids while the use of Hbd results in the (S) stereoisomer. In other embodiments, the use of PhaB results in (S)-3-hydroxyacids while the use of Hbd results in the (R) stereoisomer. In some embodiments, (S)-DHBA and/or (S)-3-HBL are produced, while in other embodiments, (R)-DHBA and/or (R)-3-HBL are produced. Methods and compositions described herein can also be applied to screen for an enzyme with similarity to hbd, with similar stereochemical preference but with an increased substrate range for the production of (R)-DHBA and (R)-3-HBL.

Optimization of protein expression may also require in some embodiments that a gene encoding an enzyme be modified before being introduced into a cell such as through codon optimization for expression in a bacterial cell. Codon usages for a variety of organisms can be accessed in the Codon Usage Database (kazusa.or.jp/codon/).

In some embodiments protein engineering can be used to optimize expression or activity of one or more enzymes associated with the invention. In certain embodiments a protein engineering approach could include determining the 3D structure of an enzyme or constructing a 3D homology model for the enzyme based on the structure of a related protein. Based on 3D models, mutations in an enzyme can be constructed and incorporated into a cell or organism, which could then be screened for an increased production of 3,4-DHBA, 2,3-DHBA and/or 3-HBL. In some embodiments production of 3,4-DHBA, 2,3-DHBA and/or 3-HBL in a cell could be increased through manipulation of enzymes that act in the same pathway as the enzymes associated with the invention. For example in some embodiments it may be advantageous to increase expression of an enzyme or other factor that acts upstream of a target enzyme such as an enzyme associated with the invention. This could be achieved by over-expressing the upstream factor using any standard method.

Methods and compositions described herein for the production of 3-HBL, 3,4-DHBA, and 2,3-DHBA from sugars and sugar-derived substrates have widespread applications. For example, 3-HBL is used in the pharmaceutical industry as a building block for cholesterol-reducing statins such as CRESTOR® and LIPITOR®, antibiotics such as ZYBOX®, the anti-hyperlipidemic medication E7EZETIMIBE® (Lee et al., 2008; Lee and Park, 2009), HIV inhibitors (Kim et al., 1995) and the nutritional supplement carnitine (Wang and Hollingsworth, 1999b).

3-HBL featured on the Department of Energy's list of top ten chemicals from biomass in a 2004 report. The annual market for statins was estimated to be $10-15 billion in 2003 and 2004, while the annual demand for L-carnitine is estimated to be several hundred metric tons. Currently, DHBA is not commercially available, while 3-HBL costs $30-100 per gram. The high cost and low availability of these compounds increases the costs of statin drugs.

Economical biochemical synthesis of DHBA and 3-HBL employing glucose (or other simple sugars derived from biomass) as the only feedstock affords an opportunity for considerably reducing the cost of statin drugs. Further, it may allow the use of these versatile building blocks for the economical synthesis of a variety of other drugs. For example, DHBA and 3-HBL can be readily derivatized into the valuable nutritional supplement L-carnitine, which has an approximate cost of $5 per gram.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

Example 1

Glycolate, DHBA and 3-HBL Synthesis in MG1655 (DE3)

Glycolate synthesis was first investigated in the E. coli K-12 strain MG1655 (DE3) transformed with pCOLADuet-ycdW-aceA-aceK in LB and minimal medium. pCOLADuet-ycdW-aceA-aceK is an IPTG inducible Duet vector which allows over-expression of the glycolate pathway enzymes YcdW, AceA and AceK. MG1655 (DE3) cells carrying pCOLADuet-ycdW-aceA-aceK, grown in minimal medium, synthesized up to 0.7 g/L of glycolate at the shake flask scale after 48 hours (as compared to a maximum of 0.25 g/L of glycolate observed in cells grown in LB) on induction with IPTG. Experiments with the same strain only expressing YcdW (off pCOLADuet-ycdW) or only YcdW and AceA (off pCOLAduet-ycdW-aceA) did not show any glycolate synthesis, indicating that co-expression of YcdW, AceA and AceK was beneficial for glycolate production.

However, the glycolate titers observed with MG1655 (De3) carrying pCOLAduet-ycdW-aceA-aceK were only observed transiently in the course of the four day fermentation and any glycolate synthesized was observed to be subsequently consumed by the cells, presumably along one or more competing glycolate consumption pathways. To verify if this transiently synthesized glycolate could be converted to 3-HBL or DHBA, MG1655 (DE3) carrying pCOLADuet-ycdW-aceA-aceK was transformed with the DHBA/3-HBL pathway plasmids (pETDuet-bktB-phaB and pCDFDuet-pct-tesB) and the resulting strain was grown in minimal medium supplemented with glucose. The resulting strain, after induction with IPTG, was expected to express the glycolate pathway and DHBA/3-HBL pathway enzymes off the three Duet vectors. However, the resulting strain synthesized neither DHBA or 3-HBL nor any glycolate. Insufficient and transient glycolate synthesis was hypothesized as the reason for the inability of this strain to effectively synthesize DHBA and 3-HBL directly from glucose.

Example 2

Glycolate Synthesis in MG1655 (DE3) ΔiclR, Δgcl, ΔaceB and MG1655 (DE3) ΔiclR, Δgcl, ΔaceB, ΔglcB using pCOLADuet-ycdW-aceA-aceK For the construction of a strain capable of sustained glycolate synthesis, the genes iclR, gcl, aceB and glcB were knocked out from MG1655 (DE3) to construct the strains MG1655 (DE3) ΔiclR, Δgcl, ΔaceB and MG1655 (DE3) ΔiclR, Δgcl, ΔaceB, ΔglcB. The iclR knockout is expected to relieve the transcriptional repression of the aceBAK operon to enhance endogenous AceA and AceK synthesis to complement the expression off pCOLADuet-ycdW-aceAa-aceK. The gcl, aceB and glcB knockouts eliminate some of the glyoxylate consumption pathways. Unlike the strains constructed in US 2009/0155867, the objective was not to construct a strain capable of maximum glycolate synthesis, but rather, to construct a strain capable of sustained glycolate synthesis that would be sufficient and optimized for DHBA synthesis. It should be noted, that since acetyl-CoA is a common intermediate for both glycolate and DHBA synthesis, a strain engineered for maximum glycolate synthesis (such as the one described in US 2009/0155867) may not necessarily be optimal for DHBA and 3-HBL synthesis.

Fermentations with MG1655 (DE3) ΔiclR, Δgcl, ΔaceB carrying pCOLAduet-ycdW-aceA-aceK in minimal medium supplemented with 0.8% (wt./vol.) glucose at 30° C., induced with 1 mM IPTG, showed sustained glycolate synthesis with glycolate titers building up to 1.5 g/L after three days. In contrast, growth in LB resulted in more modest and transient titers of about 0.25 g/L. Without wishing to be bound by any theory, reduced titers in the presence of LB may be due, at least in part, to the fact that the glyoxylate shunt is heavily repressed in the presence of readily fermentable alternative carbon sources as found in a rich medium like LB. The effect of varying glucose supplementation on glycolate synthesis was also studied and, in some embodiments, 0.8% wt/vol. glucose was found to be optimal for glycolate synthesis. In some embodiments, glucose supply concentrations higher than 0.8% result in substantially lower glycolate titers, potentially due to repression of the glyoxylate shunt in the presence of excess glucose. In some embodiments, concentrations less than 0.8% of glucose were not sufficient.

The effect of varying the IPTG inducer concentration was also studied (see Example 11).

Previous work has demonstrated production of glycolate in MG1655 strains that over-express YcdW off a plasmid, but only after 9 different genes were knocked out (aceB, gcl, glcD, glcE, glcF, aldA, iclR, eddA and eda) (US 2009/0155867). By comparison, herein, comparable titers were achieved after only knocking out 3 genes (iclR, aceB, gcl), combined with co-over-expression of YcdW, AceA and AceK, using, for example pCOLADuet. Strains described herein, with fewer knockouts than those described in the prior art, are likely to be healthier, meaning better able to grow in minimal medium and better able to co-express multiple pathway enzymes, because they have many of the anaplerotic pathways (critical for growth in minimal medium) intact.

Fermentations with MG1655 (DE3) ΔiclR, Δgcl, ΔaceB, ΔglcB with the additional glcB knockout to eliminate expression of malate synthaseG, carrying pCOLADuet-ycdW-aceA-aceK under similar conditions showed slightly lower glycolate titers of about 1.1 g/L, presumably due to adverse metabolic effects of this additional knockout to the inability of the cells to synthesize any malate.

Example 3

Assessing Fitness of MG1655 (DE3) ΔiclR, Δgcl, ΔaceB Carrying pETDuet-bktB-phaB and pCDFDuet-pct-tesB with Respect to DHBA and 3-HBL Synthesis To assess the fitness of strain MG1655 (DE3) ΔiclR, Δgcl, ΔaceB for DHBA and 3-HBL synthesis, MG1655 (DE3) ΔiclR, Δgcl, ΔaceB and MG1655 (DE3) carrying the DHBA/3-HBL pathway plasmids (pETDuet-bktB-phaB and pCDF-Duet-pct-tesB) were cultured in shake flasks in LB supplemented with 1% glucose. The objective, at least in part, was to assess if the knockouts introduced in the strain MG1655 (DE3) ΔiclR, Δgcl, ΔaceB had somehow impaired DHBA or 3-HBL synthesis. The results indicated that strains (MG1655 (DE3) ΔiclR, Δgcl, ΔaceB and MG1655 (DE3)) showed similar DHBA and 3-HBL titers at the shake flask scale, indicating that the knockouts had not in any way impaired the ability of MG1655 (DE3) ΔiclR, Δgcl, ΔaceB to synthesize DHBA and 3-HBL from glucose and glycolate.

Experiment 4

Investigating DHBA and 3-HBL Synthesis in MG1655 (DE3) ΔiclR, Δgcl, ΔaceB Carrying pCOLADuet-ycdW-aceA-aceK, pETDuet-bktB-phaB and pCDFDuet-pct-tesB in Minimal Medium MG1655 (DE3) ΔiclR, Δgcl, ΔaceB transformed with pCOLADuet-ycdW-aceA-aceK showed sustained glycolate synthesis in minimal medium supplemented with 0.8% glucose at 30° C., with titers as high as 1.5 g/L on average. In earlier experiments in our laboratory, we had observed DHBA and 3-HBL synthesis in MG1655 (DE3) carrying pETDuet-bktB-phaB and pCDFDuet-pct-tesB at the shake flask scale when supplied with 1.5 g/L of glycolate externally in addition to glucose in LB. Thus, given the observed titers of 1.5 g/L of glycolate in the MG1655 (DE3) ΔiclR, Δgcl, ΔaceB strain transformed with pCOLADuet-ycdW-aceA-aceK, it was next investigated whether this endogenously synthesized glycolate could be efficiently converted to DHBA and 3-HBL in the MG1655 (DE3) ΔiclR, Δgcl, ΔaceB strain.

MG1655 (DE3) ΔiclR, Δgcl, ΔaceB cells carrying pCO-LADuet-ycdW-aceA-aceK (glycolate pathay plasmid) were transformed with pETDuet-bktB-phaB and pCDFDuet-pct-tesB (DHBA/3-HBL pathway plasmids). It was expected that the resulting MG1655 (DE3) ΔiclR, Δgcl, ΔaceB strain carrying pCOLADuet-ycdW-aceA-aceK, pETDuet-bktB-phaB and pCDFDuet-pct-tesB would express all the pathway enzymes (YcdW, AceA, AceK, BktB, PhaB, Pct, TesB), synthesize glycolate from glucose, and convert this endogenously synthesized glycolate to DHBA. However, when this strain was grown in minimal medium supplemented with 0.8% glucose at 30° C., it did not show substantial DHBA or 3-HBL synthesis. Moreover, the cells also demonstrated negligible synthesis of glycolate (less than 0.1 g/L). Without wishing to be bound by any theory, these results suggested that the presence of the two additional DHBA pathway plasmids imposed a metabolic burden on the cells, impairing their ability to synthesize glycolate.

Example 5

Experiments Investigating Poor Acetyl-CoA Availability as a Cause of Poor Glycolate, DHBA and 3-HBL Synthesis Effect of Acetyl-CoA Levels on Glycolate Synthesis The effects of reduced acetyl-CoA availability were investigated. Unlike growth in rich medium such as LB, growth in minimal medium requires cells to synthesize all cell components from glucose (the only available carbon source). The need to synthesize cell building blocks, coupled with the burden of maintaining multiple plasmids, and expression of multiple pathway enzymes, can impose a considerable strain on cellular resources, rapidly consuming glucose and reduce the acetyl-CoA availability. Since acetyl-CoA is required for synthesis of glycolate, activation of glycolate to glycoly-CoA and subsequent condensation for formation of DHBA and 3-HBL, a limitation in its availability could potentially impair both glycolate and DHBA/3-HBL synthesis.

To determine whether reduced acetyl-CoA availability contributed to poor glycolate synthesis, MG1655 (DE3) ΔiclR, Δgcl, ΔaceB cells carrying pCOLADuet-ycdW-aceA-aceK, pETDuet-bktB-phaB and pCDFDuet-pct-tesB were grown up in minimal medium supplemented with five different concentrations of glucose: a) 0.8%; b) 1%; c) 1.25%; d) 1.5%; and e) 2%. If acetyl-CoA availability was substantially contributing to poor glycolate synthesis, then increased glucose supplementation should alleviate it. However, negligible glycolate synthesis was observed in each of the cases, indicating that limited acetyl-CoA availability was not causing poor glycolate synthesis.

Comparison of DHBA and 3-HBL Synthesis in MG1655 (DE3) ΔiclR, Δgcl, ΔaceB Carrying pETDuet-bktB-phaB and pCDFDuet-pct-tesB in LB and Minimal Medium Supplemented with Glucose and Glycolate To determine whether growth in minimal medium and resulting lower acetyl-CoA availability affect DHBA and 3-HBL synthesis in cultures where glycolate is supplied externally to the cells, MG1655 (DE3) ΔiclR, Δgcl, ΔaceB cells carrying the DHBA/3-HBL pathway plamsids pETDuet-bktB-phaB and pCDFDuet-pct-tesB were grown in a) LB supplemented with 1% glucose and b) minimal medium supplemented with 0.8% glucose. 40 mM (3.3 g/L) glycolate was supplied to each set of the cultures. For the same strain, titers of about 2 g/L of DHBA were observed in the LB cultures while titers of only about 0.34 g/L were observed in the minimal medium cultures, indicating that reduced acetyl-CoA availability in minimal medium indeed hampers DHBA and 3-HBL synthesis. Thus, while reduced acetyl-CoA availability did not appear to be a primary cause of poor glycolate synthesis in MG1655 (DE3) ΔiclR, Δgcl, ΔaceB, carrying pCOLAduet-ycdW-aceA-aceK and the DHBA/3-HBL pathway plasmids, it did appear to affect DHBA and 3-HBL synthesis.

Investigating Other Causes of Metabolic Burden

Figure 7:
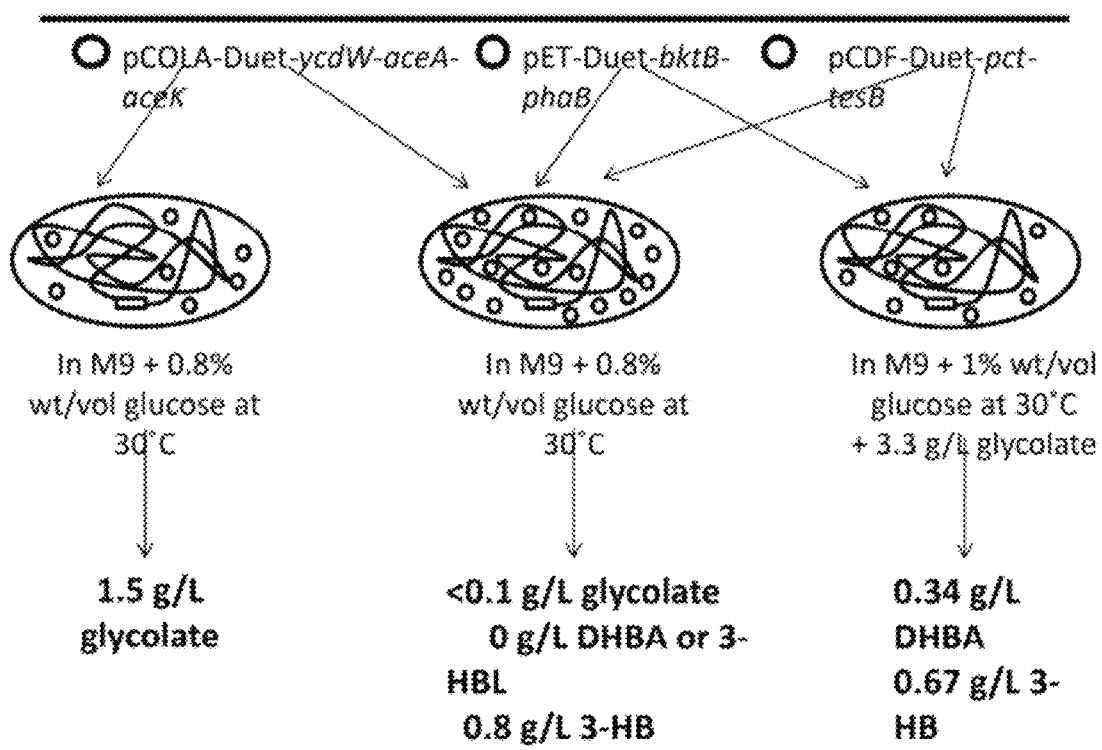
FIG. 7 presents a schematic outlining the observed metabolic burden effect.

Thus as outlined in FIG. 7, while MG1655 (DE3) ΔiclR, Δgcl, ΔaceB cells carrying the glycolate pathway plasmid pCOLADuet-ycdW-aceA-aceK produced 1.5 g/L of glycolate (at 1 mM IPTG induction level), cells carrying both glycolate and DHBA pathway plasmids produced less than 0.1 g/L of glycolate. Interestingly, a considerable amount of 3-hydroxybutyrate (3-HB) was observed to be synthesized by these cells. 3-HB is a byproduct of the metabolism of acetyl-CoA by the DHBA and 3-HBL pathway enzymes. Without wishing to be bound by any theory, these results suggested that the DHBA and 3-HB pathway enzymes were expressed in the cells and that the presence of the two additional DHBA pathway plasmids imposed a metabolic burden on the cells, specifically impairing their ability to synthesize glycolate. To determine whether the expression of the glycolate pathway enzymes was affected in the presence of DHBA pathway plasmids, the expression of all of the pathway enzymes in MG1655 (DE3) ΔiclR, Δgcl, ΔaceB carrying pCOLADuet-ycdW-aceA-aceK along with pETDuet-bktB-phaB and pCDFDuet-pct-tesB was investigated as described below.

Example 6

Expression of YcdW, AceA, AceK, BktB, PhaB, Pct and TesB in MG1655 (DE3) ΔiclR, Δgcl, ΔaceB MG1655 (DE3) ΔiclR, Δgcl, ΔaceB cells carrying pCOLADuet-ycdW-aceA-aceK, and MG1655 (DE3) ΔiclR, Δgcl, ΔaceB cells carrying pCOLADuet-ycdW-aceA-aceK along with pETDuet-bktB-phaB and pCDFDuet-pct-tesB, were grown in M9 medium supplemented with 0.8% glucose and induced with 1 mM IPTG. MG1655 (DE3) ΔiclR, Δgcl, ΔaceB cells carrying the empty vector pCOLADuet and those carrying pCOLADuet-ycdW-aceA-aceK along with pETDuet and pCDFDuet were grown up as control. Protein lysates were made 6 hours post induction and run on an SDS-Polyacrylamide gel for separation of the expressed proteins. While distinct bands, indicating over-expression of YcdW and AceA, were observed for MG1655 (DE3) ΔiclR, Δgcl, ΔaceB cells carrying only pCOLADuet-ycdW-aceA-aceK, only faint bands corresponding to YcdW and AceA were observed for MG1655 (DE3) ΔiclR, Δgcl, ΔaceB cells carrying pCOLADuet-ycdW-aceA-aceK in combination with pETDuet-bktB-phaB and pCDFDuet-pct-tesB. This strain however did show good expression of BktB, PhaB, Pct and TesB. Thus, it appeared that in the presence of the DHBA/3-HBL pathway plasmids in addition to pCOLADuet-ycdW-aceA-aceK, only the DHBA and 3-HBL pathway enzymes (BktB, PhaB, Pct and TesB) were expressed well, with minimal (if any) expression of glycolate pathway enzymes (YcdW, AceA and AceK). Without wishing to be bound by any theory, the presence of multiple plasmids in the cells may result in a metabolic burden that manifests in the form of insufficient expression of glycolate pathway plasmids that prevents effective glycolate synthesis.

It was hypothesized that such a metabolic burden may stem, at least in part, from:

i) Reduced T7 Polymerase Availability:

Distribution of T7 RNA polymerase between the multiple Duet vectors in strains carrying glycolate and DHBA/3-HBL pathway plasmids could cause reduced expression of pathway enzymes, hampering glycolate, DHBA and 3-HBL synthesis.

ii) Plasmid Instability:

During growth under metabolically stressful conditions, plasmid instability could result in mutated and/or defective copies of plasmids that no longer encode correct enzymes or have hampered expression while conferring the same antibiotic resistance as before.

Example 7

Investigating Plasmid Instability as Cause of Observed Metabolic Burden Effect

Plasmid instability can manifest in the form of a) drastic structural changes (such as those arising out of homologous recombination); and b) specific mutations that hamper expression without compromising antibiotic resistance. To determine whether plasmid instability in the form of drastic structural changes was the cause of the reduced ability to synthesize glycolate in the presence of DHBA and 3-HBL pathway plasmids, MG1655 (DE3) ΔiclR, Δgcl, ΔaceB cells carrying pCOLADuet-ycdW-aceA-aceK, pETDuet-bktB-phaB and pCDFDuet-pct-tesB were grown in minimal medium supplemented with glucose and plasmid minipreps were performed to isolate plasmids after 24 and 48 hrs post induction with 1 mM IPTG. In all cases, all three plasmids (pCOLADuet-ycdW-aceA-aceK, pETDuet-bktB-phaB and pCDFDuet-pct-tesB) were isolated and verified to be intact using restriction digests. While this did not rule out the possibility of mutations in the plasmids rendering them ineffective in expression, it did indicate that the plasmids were not undergoing drastic structural changes.

Investigating Reduced T7 Polymerase Availability as a Cause of Metabolic Burden

MG1655 (DE3) ΔiclR, Δgcl, ΔaceB carries the λDE3 prophage cassette integrated into its chromosome and synthesizes a certain amount of T7 RNA polymerase (T7 RNAP) on induction with IPTG. In an MG1655 (DE3) ΔiclR, Δgcl, ΔaceB strain carrying pCOLADuet-ycdW-aceA-aceK, pETDuet-bktB-phaB and pCDFDuet-pct-tesB, T7 RNAP in turn brings about transcription of the genes cloned into the three Duet vectors in front of T7lac promoters. The cells were expected to synthesize a certain fixed amount of T7 polymerase in response to induction with IPTG. In MG1655 (DE3) ΔiclR, Δgcl, ΔaceB, carrying only pCOLADuet-ycdW-aceA-aceK, this T7 RNAP was expected to be distributed amongst the two T7lac promoter sites in front of ycdW and aceA-aceK respectively. On the other hand, in the presence of the three different Duet vectors (pCOLADuet-ycdW-aceA-aceK, pETDuet-bktB-phaB and pCDFDuet-pct-tesB), this same amount of T7 RNAP is now distributed amongst the 6 T7lac promoter sites. Thus the effective T7 RNAP available to initiate transcription from each promoter is substantially reduced (at least 3 fold), thereby affecting expression of the corresponding genes cloned in front of these promoters. Moreover, expression off the Duet vector with the lower copy number was expected to suffer the most. Thus reduced T7 polymerase availability was expected to affect expression of pathway enzymes and hence synthesis of glycolate, DHBA and 3-HBL. This hypothesis was investigated through the following experiments.

Example 8

Promoter Deletion of ΔT7lac-pETDuet and ΔT7lac-pCDFDuet Vectors

T7lac promoter region was Deleted from the pETDuet and pCDFDuet vectors to construct the plasmids ΔT7lac-pETDuet and ΔT7lac-pCDFDuet. Glycolate synthesis was then studied in the following strains.

Figure 8:
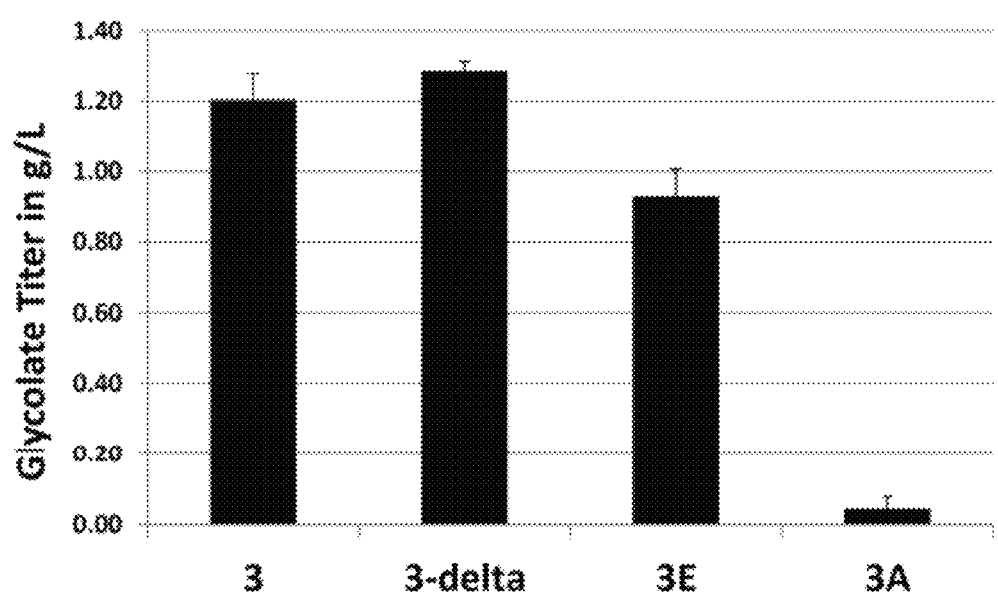
FIG. 8 presents a graph depicting T7 RNA polymerase availability, which was revealed to be a limiting factor for expression of glycolate pathway enzymes and glycolate synthesis under metabolically stressful conditions. Strain 3=MG1655 (DE3) ΔiclR, ΔaceB carrying pCOLADuet-ycdW-aceA-aceK; Strain 3-delta=MG1655 (DE3) ΔiclR, ΔaceB carrying pCOLADuet-ycdW-aceA-aceK, ΔT7lac-pETDuet and ΔT7lac-pCDFDuet; Strain 3E=MG1655 (DE3) ΔiclR, Δgcl, ΔaceB carrying pCOLADuet-ycdW-aceA-aceK, pETDuet and pCDFDuet; and Strain 3A=MG1655 (DE3) ΔiclR, Δgcl, ΔaceB carrying pCOLADuet-ycdW-aceA-aceK, pETDuet-bktB-phaB and pCDFDuet-pct-tesB.
Figure 9:
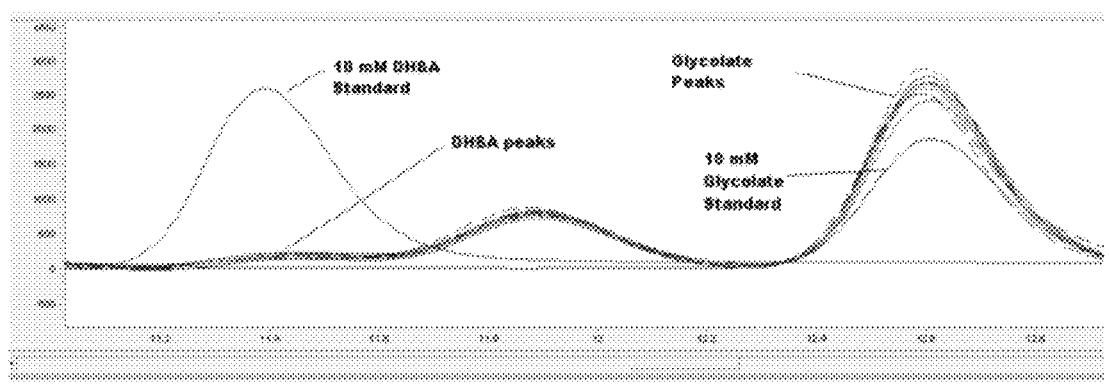
FIG. 9 reveals an HPLC time trace indicating DHBA synthesis in MG1655 (DE3) ΔiclR, Δgcl, ΔaceB carrying pHHD01K-ycdW-aceA-aceK, pETDuet-bktB-phaB and pCDFDuet-pct-tesB.

1. Strain 3: MG1655 (DE3) ΔiclR, Δgcl, ΔaceB carrying pCOLADuet-ycdW-aceA-aceK
2. Strain 3-delta: MG1655 (DE3) ΔiclR, Δgcl, ΔaceB carrying pCOLADuet-ycdW-aceA-aceK, ΔT7lac-pETDuet and ΔT7lac-pCDFDuet
3. Strain 3E: MG1655 (DE3) ΔiclR, Δgcl, ΔaceB carrying pCOLADuet-ycdW-aceA-aceK, pETDuet and pCDFDuet
4. Strain 3A: MG1655 (DE3) ΔiclR, Δgcl, ΔaceB carrying pCOLADuet-ycdW-aceA-aceK, pETDuet-bktB-phaB and pCDFDuet-pct-tesB Each of these strains were grown in minimal medium supplemented with 0.8% glucose and induced using 1 mM IPTG after reaching an O.D$_{600}$ of about 0.6. As observed from FIG. 8, just as before, the strain carrying only pCOLADuet-ycdW-aceA-aceK (Strain 3) synthesized about 1.3 g/L of glycolate, while the strain carrying pCOLADuet-ycdW-aceA-aceK, pETDuet-bktB-phaB and pCDFDuet-pct-tesB (Strain 3A) made negligible glycolate (less than 0.1 g/L). On the other hand the strain carrying the empty pETDuet and pCDFDuet plasmids (Strain 3E) made only about 0.9 g/L of glycolate. While these empty plasmids do not contain any genes, they still have intact T7lac promoter sites which can recruit T7 RNAP, reducing its availability for expression off pCOLADuet-ycdW-aceA-aceK.

By comparison, the strain carrying pCOLADuet-ycdW-aceA-aceK, ΔT7lac-pETDuet and ΔT7lac-pCDFDuet (Strain 3-delta) made roughly 1.3 g/L of glycolate (similar to the strain only carrying pCOLADuet-ycdW-aceA-aceK). While these plasmids impose similar metabolic burden associated with plasmid maintenance as the empty vectors, the lack of T7lac promoter sites prevents T7 RNAP sequestration by these plasmids. As a result, all the T7 RNAP synthesized in this strain is exclusively available for expression off pCOLADuet-ycdW-aceA-aceK. As a result, this strain synthesizes 1.3 g/L of glycolate. These results supported the hypothesis that T7 RNAP sequestration by pETDuet-bktB-phaB and pCDFDuet-pct-tesB affects expression of the glycolate pathway genes off pCOLADuet-ycdW-aceA-aceK, preventing effective glycolate synthesis.

Example 9

Construction of pHHD0K-ycdW-aceA-aceK Plasmid

One approach investigated for overcoming the T7 RNAP availability problem was to distribute the DHBA/3-HBL and glycolate pathway plasmids between two independently inducible expression systems. This can be achieved by replacing the T7 polymerase dependent glycolate pathway plasmid pCOLADuet-ycdW-aceA-aceK by cloning the glycolate pathway genes into a vector system that allows expression independent of T7 RNAP. This would decouple the two pathways, increase the T7 polymerase available for the DHBA plasmids (pETDuet-bktB-phaB and pCDFDuet-pct-tesB) and allow independent control and reliable expression of the glycolate pathway enzymes by varying the concentration of the inducer molecule. The pKVS45 vector has a p15 origin of replication compatible with pETDuet-bktB-phaB and pCDFDuet-pct-tesB in terms of co-replication. It contains a multicloning site preceded by a tetracycline or anhydro-tetracycline (aTc) inducible Tet promoter.

This plasmid confers resistance to ampicillin. To ensure compatibility with existing DHBA pathway plasmids, a segment containing the origin of replication and Tet promoter and gene was PCR amplified and ligated with a Kanamycin resistance cassette to create the plasmid pHHD01K. Since the plasmid only contains a single multi-cloning site, the genes ycdW, aceA and aceK were combined into an artificial operon similar to the naturally occurring aceBAK operon in structure. The artificial operon was constructed using SOEing (Splicing by Overlap Extension) polymerase chain reaction of the individual PCR amplified genes. The resulting ycdW-aceA-aceK operon was cloned into the multiple cloning site of pHHD01K to create the glycolate pathway plasmid pHHD01K-ycdW-aceA-aceK.

Example 10

Glycolate, DHBA and 3-HBL Synthesis in MG1655 (DE3) ΔiclR, Δgcl, ΔaceB Carrying pHHD01K-ycdW-aceA-aceK as the Glycolate Pathway Plasmid Transformation of MG1655 (DE3) ΔiclR, Δgcl, ΔaceB with the newly constructed glycolate pathway plasmid, pHHD01K-ycdW-aceA-aceK in minimal medium supplemented with 0.8% glucose at 30° C. with varying concentrations of aTc resulted in titers of about 1.5 g/L for induction levels of 250 ng/ml to 500 ng/ml. Moreover, MG1655 (DE3) ΔiclR, Δgcl, ΔaceB cells transformed with pHHD01K-ycdW-aceA-aceK, and DHBA pathway plasmids (pETDuet-bktB-phaB and pCDFDuet-pct-tesB), cultured in minimal medium supplemented with 0.8% glucose, on induction with 100 ng/ml, 250 ng/ml and 500 ng/ml aTc and 1 mM IPTG, made up to 1 g/L of glycolate even in the presence of the DHBA plasmids. This indicated that the strategy of replacing pCOLAduet-ycdW-aceA-aceK with pHHD01K-ycdW-aceA-aceK to achieve reliable expression of the glycolate pathway enzymes had been successful. Further, these strains also synthesized up to 0.12 g/L DHBA.

This represented the first demonstration of synthesis of DHBA solely from glucose. Thus, the strategy of relieving the metabolic burden by distributing the DHBA/3-HBL and glycolate pathway genes was not only successful in achieving reliable expression of all pathway enzymes, but was also critical in allowing synthesis of DHBA solely from glucose.

Example 11

Investigating Optimal Inducer Concentrations

Under metabolically stressful conditions (such as growth in minimal medium), controlling the expression of pathway enzymes is critical from the point of view of optimal distribution of cellular resources towards sustaining necessary life processes and expressing various pathway enzymes for effective product synthesis. While high inducer levels can achieve good enzyme expression, they may deplete pools of critical metabolites such as acetyl-CoA, reducing pathway fluxes and product titers. Thus, optimizing the levels of inducers is critical.

Since the level of induction by aTc was observed to have negligible effect on the DHBA concentration for aTc concentrations between 100 to 500 ng/ml, an aTc concentration of 250 ng/ml was selected for induction to study the effect of IPTG inducer concentration. MG1655 (DE3) ΔiclR, Δgcl, ΔaceB cells transformed with pHHD01K-ycdW-aceA-aceK, pETDuet-bktB-phaB and pCDFDuet-pct-tesB, were cultured in minimal medium supplemented with 0.8% glucose (50 ml cultures) and induced 250 ng/ml of aTc and varying concentrations of IPTG (100 μM, 500 μM and 1000 μM). The following results were obtained.

TABLE 1

Glycolate, DHBA and 3HBL Titers

| | Conc. Glycolate g/L | Conc. of DHBA g/L | Conc. of 3HBL in g/L | Conc of Acetate in g/L | Conc of 3HB in g/L |
|---|---|---|---|---|---|
| DHBA Plasmids | | | | | |
| 100 μM | 0.88 ± 0.15 | 0.21 ± 0.05 | 0.03 ± 0.01 | 0.45 ± 0.07 | 0.17 ± 0.02 |
| 500 μM | 0.47 ± 0.06 | 0.14 ± 0.03 | 0.00 ± 0.00 | 0.75 ± 0.06 | 0.22 ± 0.02 |
| 1000 μM | 0.30 ± 0.07 | 0.09 ± 0.02 | 0.00 ± 0.00 | 0.84 ± 0.10 | 0.20 ± 0.03 |
| Empty DHBA Plasmids | | | | | |
| 100 μM | 1.60 ± 0.14 | 0.00 ± 0.00 | 0.00 ± 0.00 | 0.59 ± 0.01 | 0.00 ± 0.00 |
| 500 μM | 1.26 ± 0.24 | 0.00 ± 0.00 | 0.00 ± 0.00 | 0.36 ± 0.13 | 0.00 ± 0.00 |
| 1000 μM | 1.11 ± 0.02 | 0.00 ± 0.00 | 0.00 ± 0.00 | 0.34 ± 0.06 | 0.00 ± 0.00 |

Figure 10:
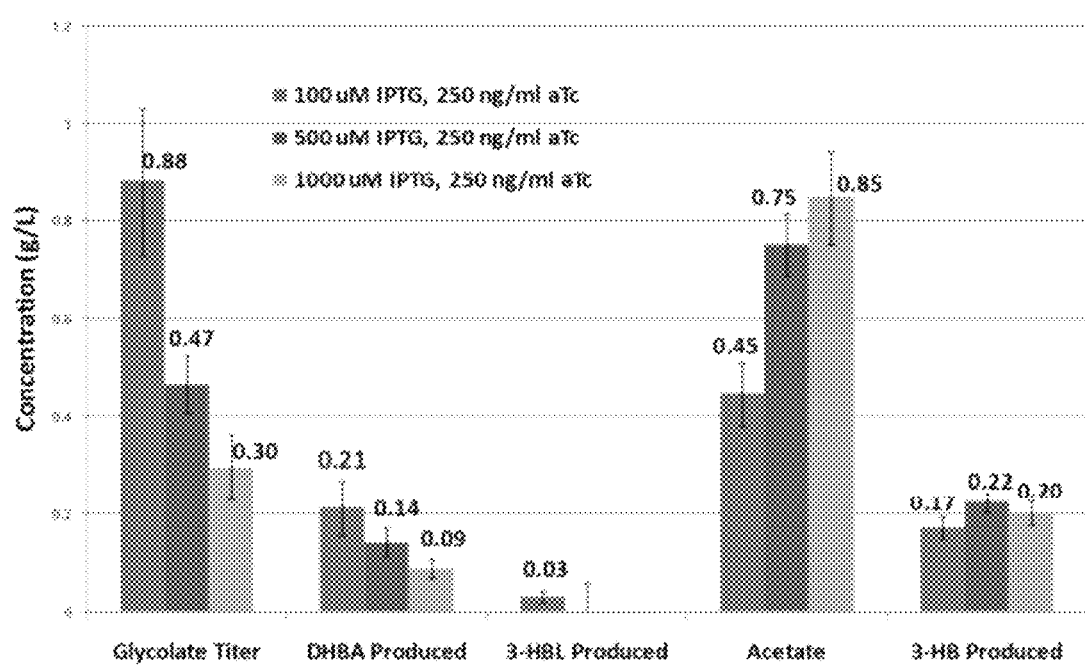
FIG. 10 presents a graph demonstrating the effect of varying IPTG inducer concentration on DHBA synthesis in MG1655 (DE3) ΔiclR, Δgcl, ΔaceB carrying pHHD01K-ycdW-aceA-aceK, pETDuet-bktB-phaB and pCDFDuet-pct-tesB.

As observed from the table above and FIG. 10, highest DHBA titers of 0.21 g/L were observed for an IPTG concentration of 100 μM. As described earlier (in Example 5), the supply glucose concentration affects acetyl-CoA availability which in turn influences DHBA and 3-HBL synthesis. In minimal medium supplied with glycolate and 0.8% glucose, MG1655 (DE3) ΔiclR, Δgcl, ΔaceB cells transformed with pETDuet-bktB-phaB and pCDFDuet-pct-tesB produced about 0.34 g/L of DHBA. Thus, the titer of 0.21 g/L was improved to 0.34 g/L and can likely be improved further by further reducing the metabolic burden by promoter replacements as discussed later. Titers can also be enhanced by enhancing acetyl-CoA availability.

Example 12

Investigating Optimal Glucose Concentrations

To investigate the effect of increased acetyl-CoA availability, fermentations were executed with varying amounts of glucose supplied to the cultures. MG1655 (DE3) ΔiclR, Δgcl, ΔaceB cells transformed with pHHD01K-ycdW-aceA-aceK, pETDuet-bktB-phaB and pCDFDuet-pct-tesB, were cultured in minimal medium supplemented with varying amounts of glucose (0.6%, 0.8%, 1%, 1.5%) and induced using 250 ng/ml of aTc and 100 µM IPTG. As expected, with increasing glucose concentrations, the DHBA titers were observed to increase (as observed from FIG. 5) with increasing supply glucose concentration.

While increasing glucose supply concentrations enhances acetyl-CoA availability for glycolate and DHBA synthesis, it also increases fluxes towards by unwanted products. Excessive glucose can also repress the glyoxylate shunt and glycolate synthesis. Thus, glucose supply concentration can be optimized to achieve selective DHBA and 3-HBL synthesis.

TABLE 2

Optimization of glucose concentration

| % Feed Glucose | Glucose supplied in g/L | Total Moles of DHBA + 3-HBL per Mole of Glucose Supplied | Moles of 3-HB per Mole of Glucose Supplied | Moles of Acetate per Mole of Glucose Supplied |
|---|---|---|---|---|
| 0.80% | 8 | 0.055 | 0.054 | 0.251 |
| 1.00% | 10 | 0.180 | 0.088 | 0.279 |
| 1.25% | 12.5 | 0.168 | 0.077 | 0.199 |
| 1.50% | 15 | 0.151 | 0.078 | 0.186 |

The above table shows that while the total moles of DHBA and 3-HBL were observed to increase with increasing amounts of glucose supplied to the cells, in some embodiments, an optimal selectivity is observed at about 1% supply concentration of glucose. From the table, the observed yield on glucose on a molar basis was about 18%. The theoretical yield on glucose (neglecting biomass accumulation and by product formation) was about 44%. Thus, in some embodiments, the yield represents only about 27% of the theoretical maximum. Further enhancements in the yield may be achieved by reducing the metabolic burden of maintaining multiple plasmids. In some embodiments, DHBA pathway enzymes are encoded by heterologous genes and thus are expressed off plasmids. However, in some embodiments, ycdW, aceA and aceK are endogenous E. coli genes and thus can be expressed directly off the chromosome by replacing the native promoters preceding these genes with constitutive promoters of specific strength to achieve required expression.

Example 13

Replacing ycdW and aceA-aceK Promoters to Achieve Chromosomal Expression to Further Relieve Metabolic Burden The native promoters and ribosome binding sites (RBSs) preceding the gene ycdW and the genes aceA-aceK in the chromosome of MG1655 (DE3) ΔiclR, Δgcl, ΔaceB, are replaced with constitutive promoters from the Anderson Promoter Library and RBSs from the Registry of Standard Biological Parts (partsregistry.org). The objective is to construct a strain capable of expressing YcdW, AceA and AceK at sufficiently high levels to eliminate the need to maintain multiple copies of the glycolate pathway plasmid pHHD01K-ycdW-aceA-aceK for YcdW, AceA and AceK expression.

Example 14

Platform Pathway for the Microbial Synthesis of 3-Hydroxyalkanoic Acids Using the Ability of the Beta-Ketothiolases to Effect Carbon-Carbon Bond Formation Reactions Between Precursor Acid Molecules One purpose of the technology described herein is to provide a general microbial biosynthetic route for the simultaneous production of a variety of structurally different 3-hydroxyalkanoic acids in cells such as E. coli cells using the unique ability of beta-ketothiolases to effect Claisen condensation reactions in alternative ways between various precursor acids for carbon-carbon bond formation. Aspects of the invention illustrate this unique carbon-carbon bond forming potential of biosynthetic beta-ketothiolase enzymes (such as BktB from Ralstonia eutropha) in the context of simultaneous microbial synthesis of the valuable chemicals, 2,3-dihydroxyacid (2,3-DHBA) and 3,4-dihydroxybutyric acid (3,4-DHBA) from glucose.

Figure 15:
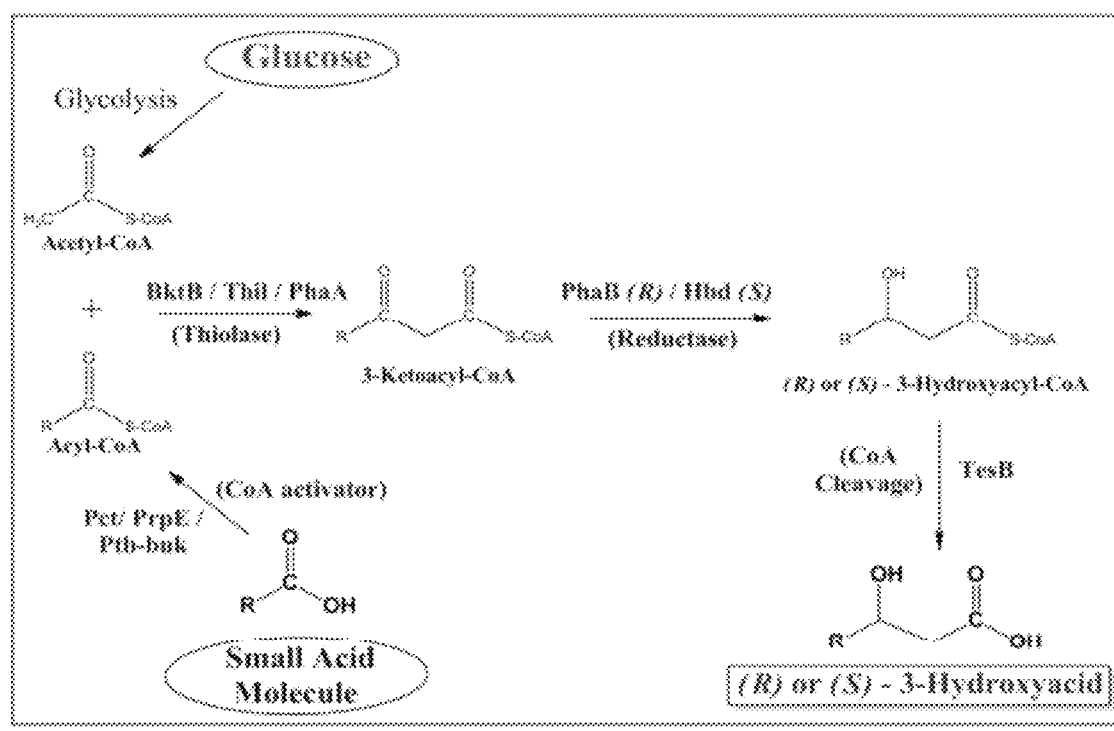
FIG. 15 presents a pathway for synthesis of 3-hydroxyalkanoic acids.

The present invention provides methods for the biosynthesis of a variety of 3-hydroxyalkanoic acids using the ability of biosynthetic thiolase enzymes to catalyze a Claisen condensation reaction for carbon-carbon bond formation in alternative ways between any two CoA thioesters derived from respective precursor small acid molecules to form structurally different 3-hydroxyalkanoic acids. The 3-hydroxyacid synthesis pathway described in a WO/2010/101651 (Martin et al.) and depicted schematically in FIG. 15 employs 4 enzymes: 1) CoA activator, 2) thiolase, 3) reductase and 4) thioesterase and depends on a Claisen condensation between acetyl-CoA and a CoA thioester (derived by CoA activation of a small acid molecule) catalyzed by a biosynthetic thiolase for the synthesis of various 3-hydroxyalkanoic acids.

Figure 16:
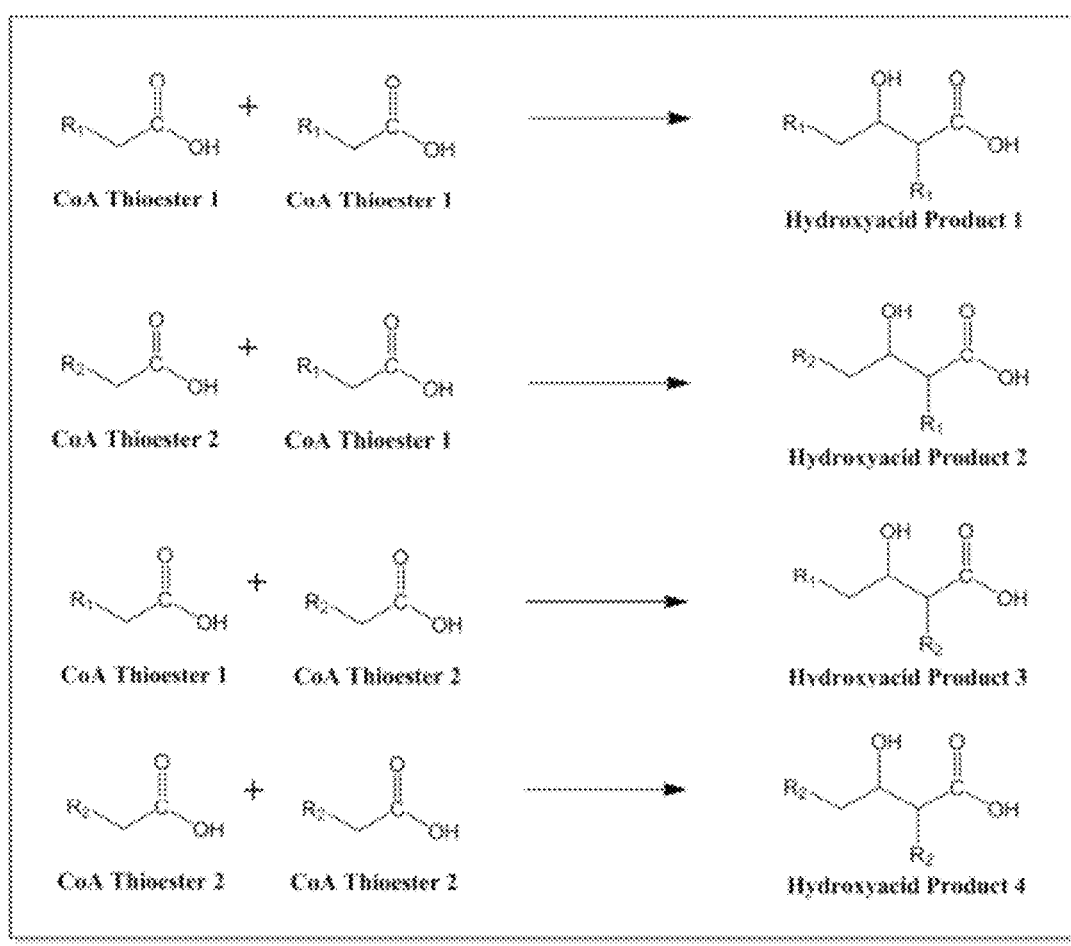
FIG. 16 shows synthesis of various hydroxyacid products via various Claisen condensation reactions between two CoA thioesters.
Figure 17:
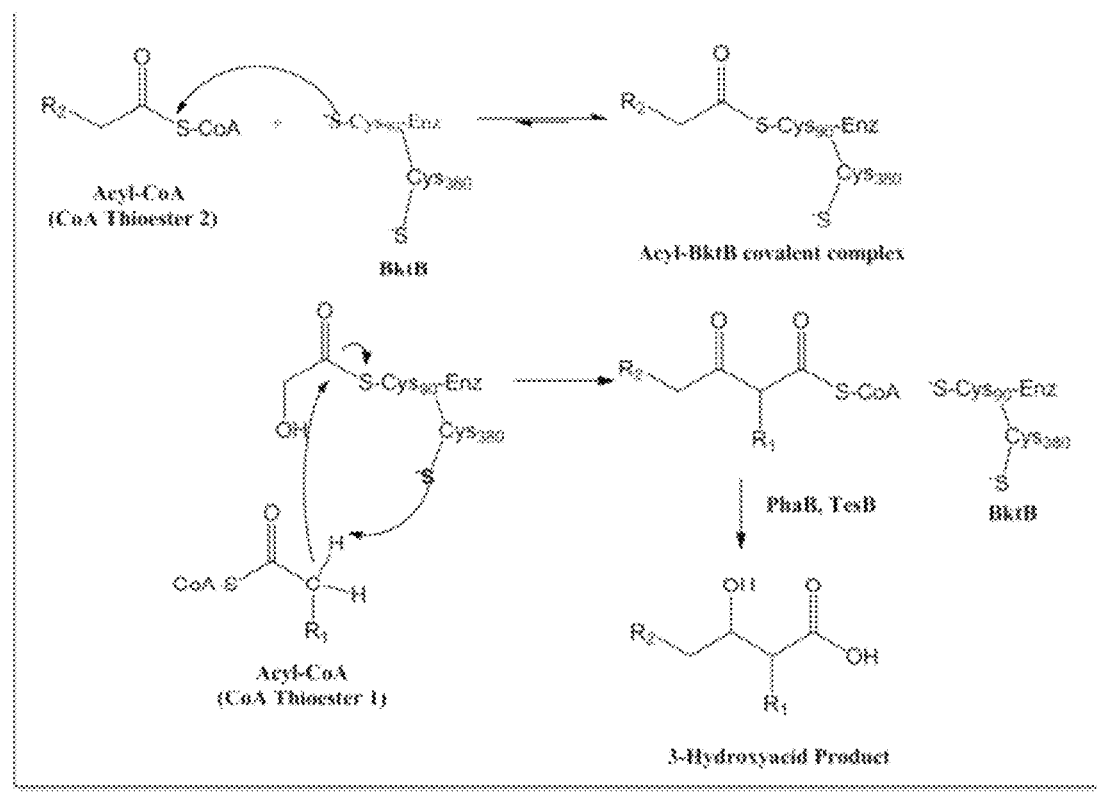
FIG. 17 shows a generalized mechanism for Type I Claisen condensation reaction between two CoA thioesters.

The initial Claisen condensation reaction catalyzed by the biosynthetic thiolase enzyme is a carbon-carbon bond formation and in general can take place between any two CoA activated small acid molecules. FIG. 16 demonstrates 4 alternative reaction products resulting from various condensation reactions in a mixture of two different CoA thioesters (R1-(CO)—S—CoA and R2-(CO)—S—CoA) that result in four different 3-ketoacyl-CoA intermediates. The keto group in these intermediates can then be reduced stereospecifically by a reductase to form the corresponding 3-hydroxyacyl-CoA intermediates. CoA cleavage by a thioesterase enzyme (such as TesB from E. coli) finally gives the corresponding 3-hydroxyalkanoic acids and hence governs the chemical structures of the final 3-hydroxyalkanoic acids synthesized using this pathway and the overall product distribution.

Figure 18:
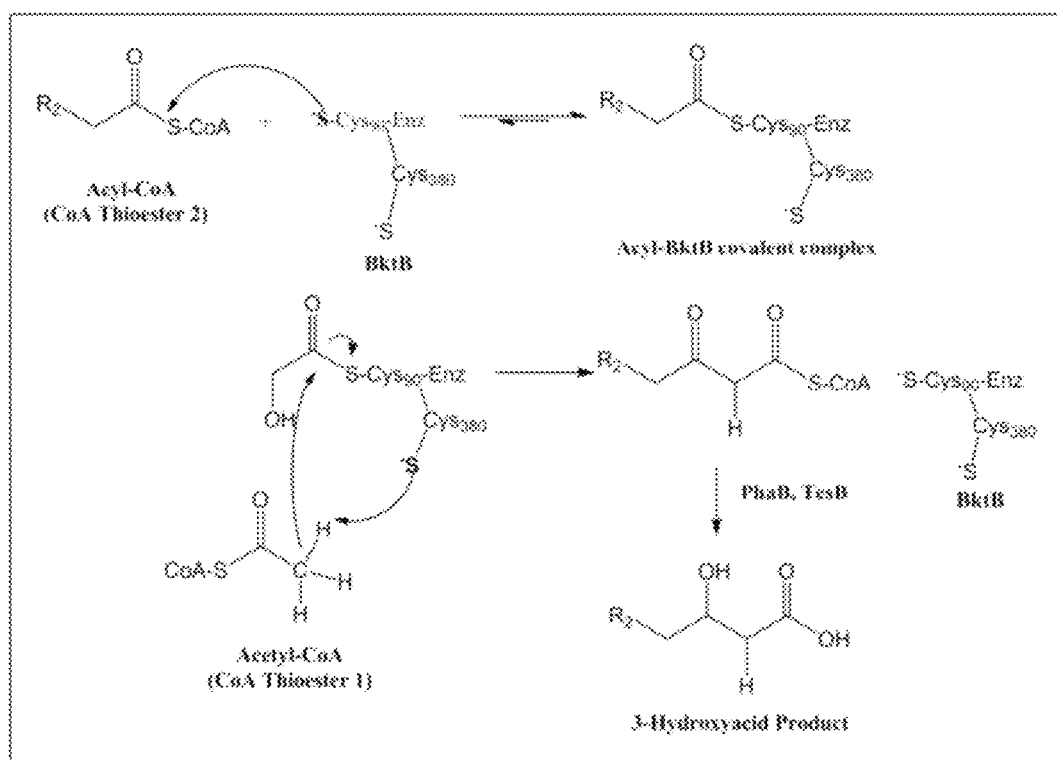
FIG. 18 shows a generalized mechanism for Type-I Claisen condensation reaction between acetyl-CoA and a CoA thioester.
Figure 19:
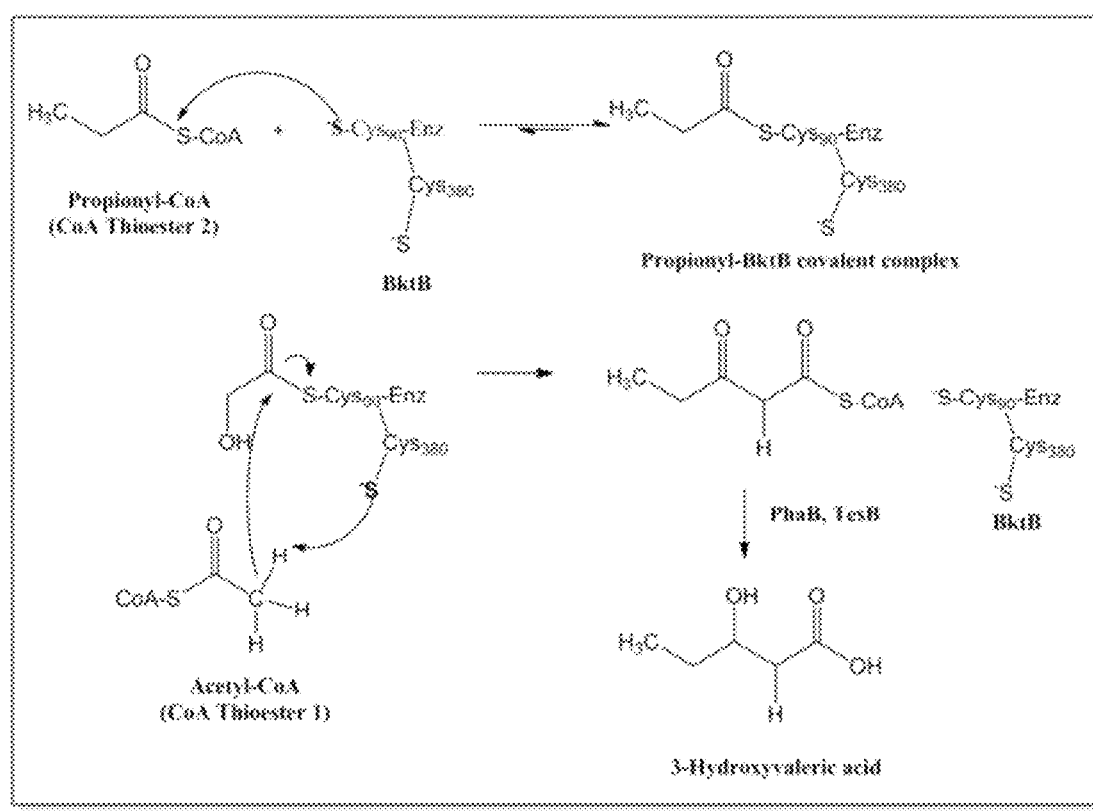
FIG. 19 shows synthesis of 3-hydroxyvaleric acid via Type I Claisen condensation reaction.

While in theory these 4 different products may be hypothesized to be formed from the condensation of any two CoA thioesters (as shown in FIG. 16), in reality the enzyme catalyzed synthesis of these products is expected to be limited by the accommodation of the substrates in the enzyme active site as well as the propensity of the substrates to participate in the different steps of catalysis depending on their chemical nature. In this sense, the thiolase is the key pathway enzyme that governs the chemical structures of the final 3-hydroxyalkanoic acids synthesized and the overall product distribution. Indeed, known natural reactions catalyzed by biosynthetic thiolases (in pathways such as polyhydroxyalknoate synthesis, butanol synthesis and isoprenoid biogenetic pathways) are typically limited to condensation of acetyl-CoA as one of the thioesters (R1=H) either with itself (to form 3-hydroxybutyric acid) or another small acid CoA thioester to form the corresponding 3-hydroxyalkanoic acid. FIG. 18 illustrates the general mechanism of this reaction (Masamune et al, 1989) involving acetyl-CoA (R1=H) as one of the thioesters condensing with Acyl-CoA (CoA Thioester 2), catalyzed by BktB (the betaketothiolase from the poly-3-hydroxybutyrate and poly-3-hydroxybutyrate-co-3-hydroxyvalerate synthesizing organism *R. eutropha*). For propionyl-CoA (R2=CH3), this condensation results in the formation of 3-ketovaleryl-CoA (precursor for 3-hydroxyvalerate). Key steps in this reaction mechanism involve a) a nucleophilic attack by the sulfur atom of residue Cys90 in BktB onto propionyl-CoA to form a propionyl-enzyme complex and b) a subsequent α-proton abstraction from acetyl-CoA by Cys380 and a nucleophilic attack by the results acetyl-CoA derived carbanion that results in the condensation product 3-ketovaleryl-CoA (as showed in FIG. 19). Similarly, 3-hydroxybutyrate is formed as a pathway by-product by the condensation of two acetyl-CoA molecules (with R1=H in Product 1, FIG. 16). Herein, the reactions involving abstraction of an α-proton from acetyl-CoA are referred to as Type I condensation reactions.

Figure 20:
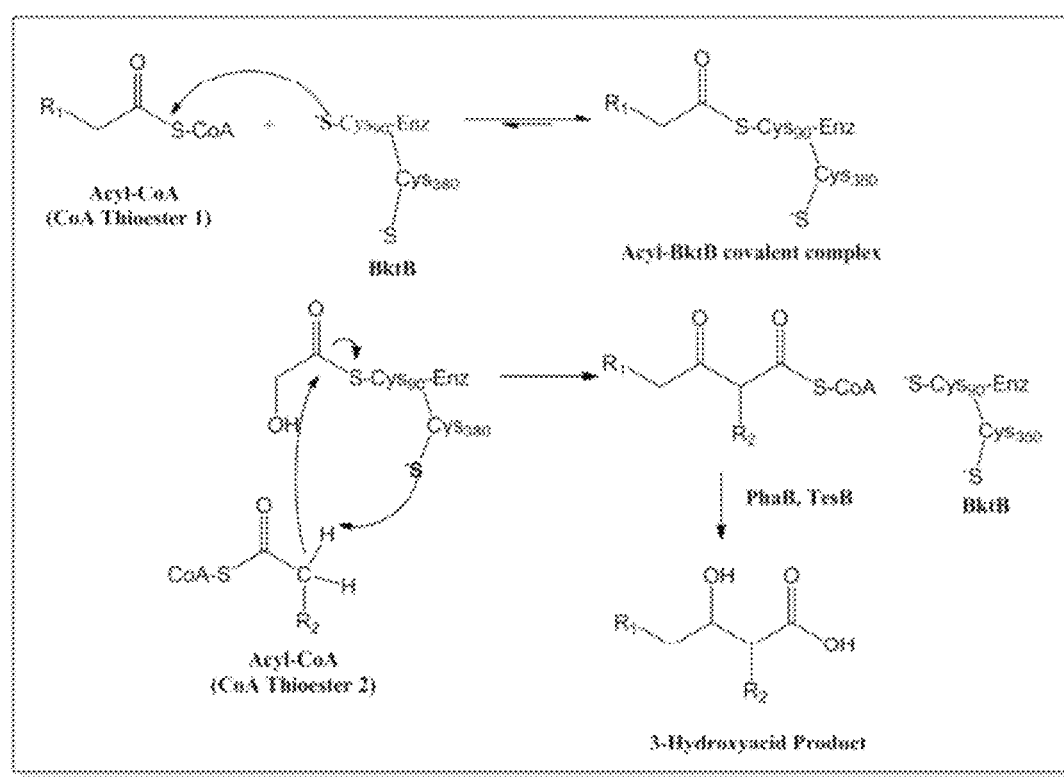
FIG. 20 shows a generalized mechanism for the Type II Claisen condensation reaction between two CoA thioesters.
Figure 21:
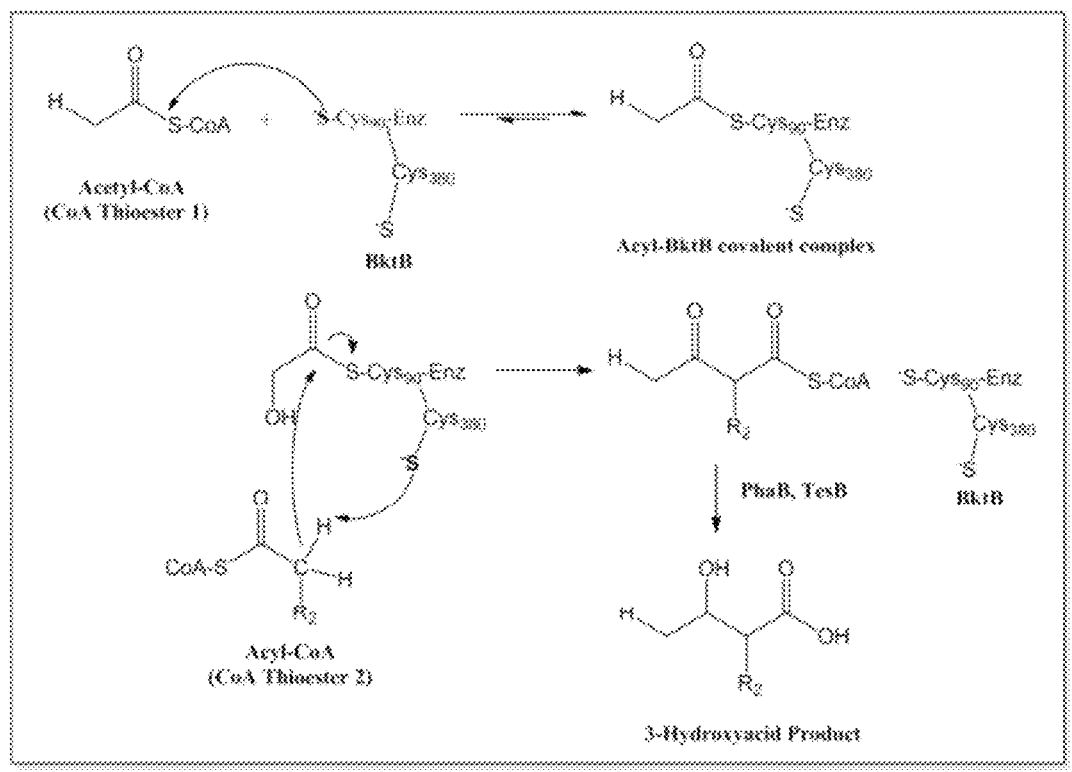
FIG. 21 shows a mechanism for the Type II Claisen condensation reaction between acetyl-CoA and Acyl-CoA.

The products of the Type II condensation reaction (Products 3 and 4 of FIG. 16, the formation of which would involve abstraction of an α-proton from the other CoA thioester (instead of acetyl-CoA) as shown in FIGS. 20 and 21) have not been reported previously. For example, a reverse condensation between propionyl-CoA and acetyl-CoA would lead to the formation of 2-methyl-3-ketobutyryl-CoA and eventually 2-methyl-3-hydroxybutyrate or condensation between two propionyl-CoAs would give 2-methyl-3-ketohexanoyl-CoA and 2-methyl-3-hydroxyhexanoic acid as the final product. While these reactions are possible, the likelihood of these reactions depends on the ease of abstraction of an α-proton from propionyl-CoA as well as favorable interactions of the resulting carbanion with the active site. Indeed, these Type H condensation reactions (defined herein as those involving abstraction of an α-proton from CoA thioesters other than acetyl-CoA) open up avenues towards microbial synthesis of a variety of structurally different 3-hydroxyalkanoic acids and extend the array of products that may be synthesized using the 3-hydroxylkanoic acid pathway well beyond those that may be simply accessed by Type I condensation reactions dependent on abstraction of protons from acetyl-CoA.

Example 15

Production of 2,3-DHBA in Addition to 3,4-DHBA

Figure 22:
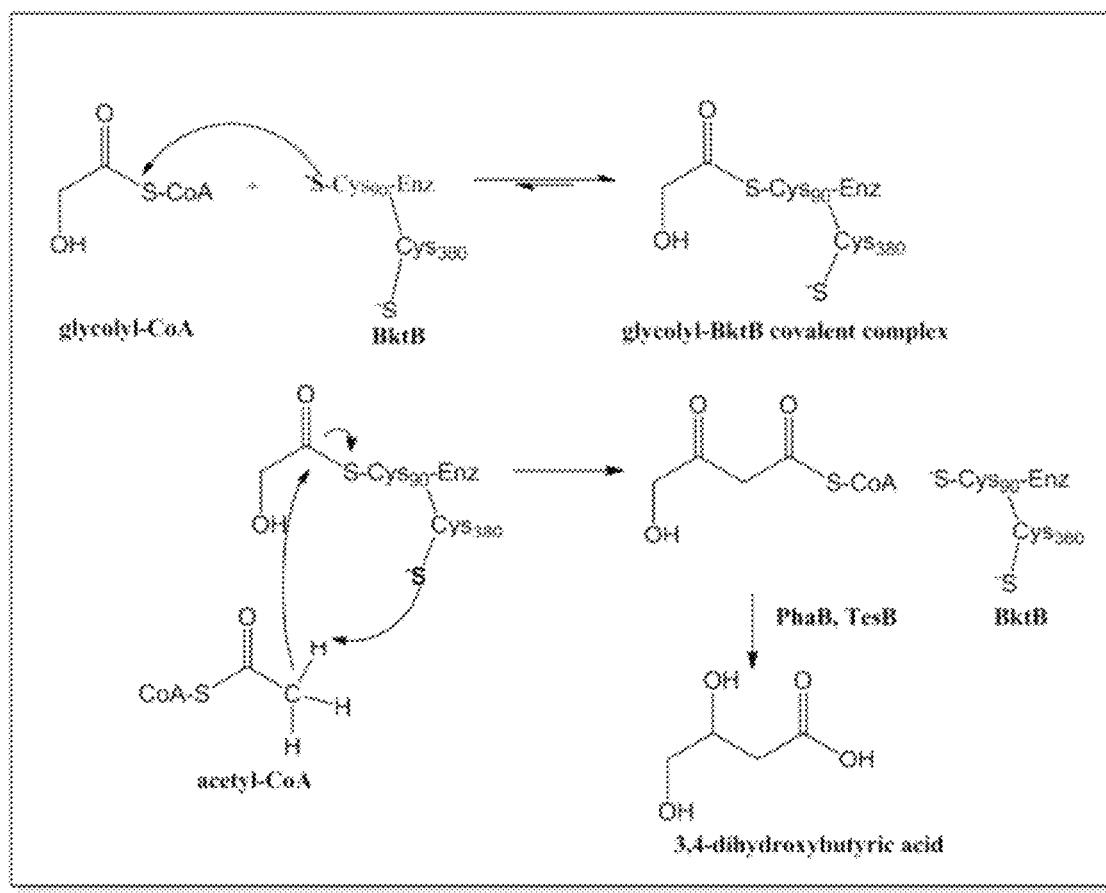
FIG. 22 shows a mechanism for formation of 3,4-dihydroxybutyric acid via the Type I Claisen condensation reaction between acetyl-CoA and glycolyl-CoA.
Figure 23:
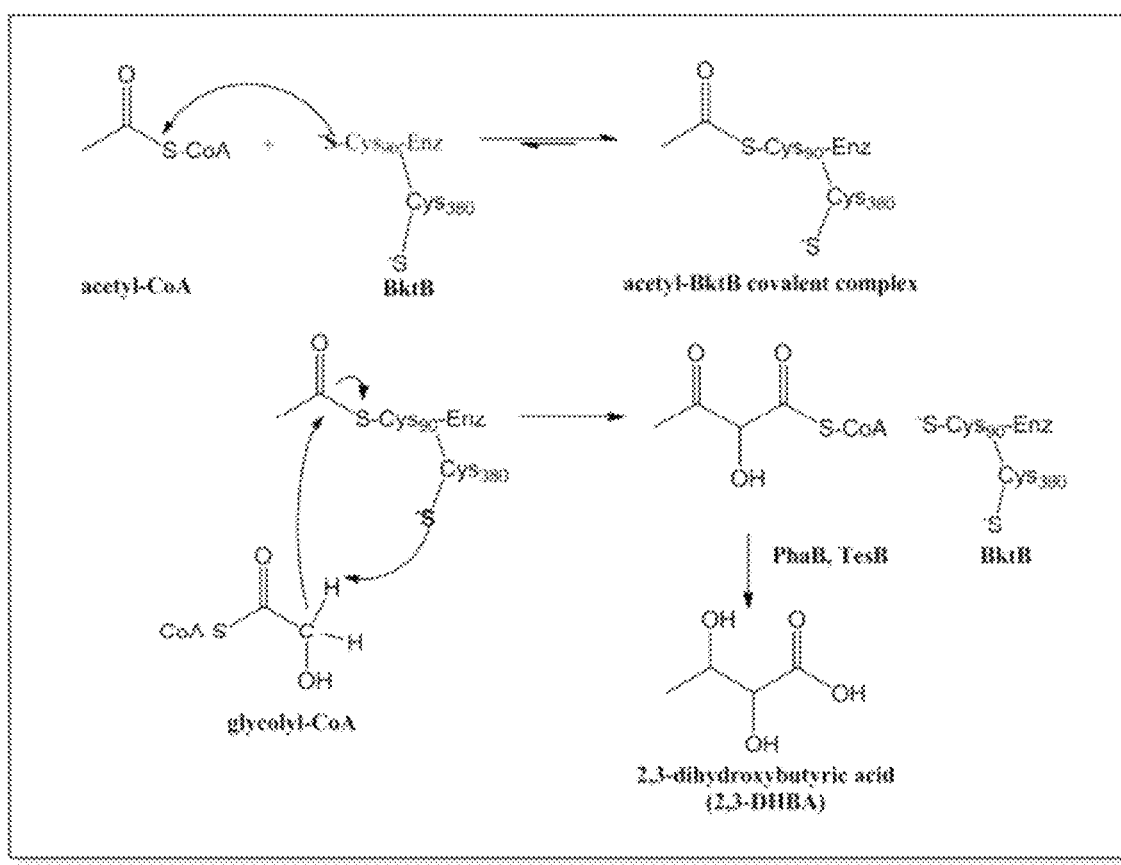
FIG. 23 shows a mechanism for formation of 2,3-dihydroxybutyric acid via Type H Claisen condensation reaction between acetyl-CoA and glycolyl-CoA.

Here, the first instance of such a Type II reaction by the beta-ketothiolase BktB is reported. It is demonstrated herein that *E. coli* cells expressing BktB as a biosynthetic thiolase (along with the other 3-hydroxyacid synthesis pathway enzymes: Pct as a CoA activator, PhaB as a reductase and TesB as a thioesterase), fed with glycolate, synthesized 2,3-dihydroxybutyric acid (2,3-DHBA) as a product formed from a Type II condensation between glycolyl-CoA and acetyl-CoA (FIG. 22) as well as forming 3,4-dihydroxybutyric acid (3,4-DHBA) due to a Type I condensation reaction (FIG. 23). 3-hydroxybutyric acid (3-HB) was also synthesized due to direct condensation between two acetyl-CoA molecules. While we have not yet detected the product of the reverse condensation between two glycolyl-CoA molecules (2,3,4-trihydroxybutyric acid), the formation of this species cannot be ruled out. This first-time demonstration of the Type II condensation reaction between CoA thioesters now opens avenues towards synthesis of a variety of structurally diverse 3-hydroxyalkanoic acids.

Detection of 2,3-DHBA in Addition to 3,4-DHBA

To test for synthesis of 3,4-DHBA, glycolate (40 mM) was fed to MG1655(DE3) ΔendA ΔrecA cells carrying pathway plasmids capable of expressing Pct (Activator to activate glycolate to glycolyl-CoA), BktB (Thiolase, to bring about Claisen condensation), PhaB (Reductase to reduce keto group) and TesB (Thioestersae to cleave CoA from 3,4-DHBA-CoA to give 3,4-DHBA). Supernatants from the culture medium were analyzed using:

a) HPLC: An Aminex H-87 column was used with 5 mM sulfuric acid at a flow rate of 0.6 ml/min. The 3,4-DHBA standard was detected at 11.45 mins on this column using a RID.

b) LC/MS: 25 mM ammonium formate (pH=2) was used as the mobile phase at a flow rate of 0.6 ml/min with the same Aminex H87 column. The MS was set to detect ions of m/z 138.1 corresponding to the expected mass of 3,4-DHBA ammonium adduct.

Figure 11:
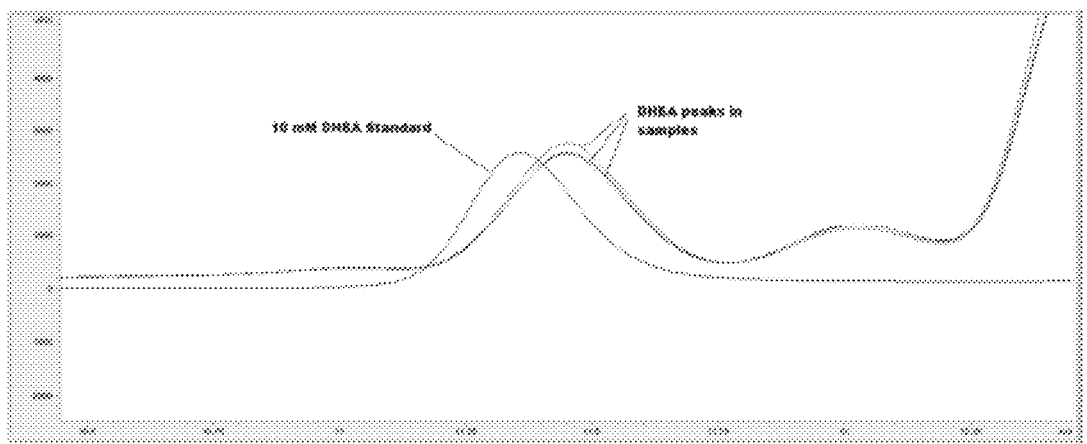
FIG. 11 presents DHBA peaks observed on LC for day 3 samples with Pct as the activator and PhaB as the reductase ("DHBA peaks in samples" denotes triplicates). A 10 mM 3,4-DHBA standard is also shown.

As observed from the LC time trace in FIG. 11, there was a discrepancy of about 0.07 mins between the DHBA sample peaks and the standard. Also, the DHBA peak was not a perfect symmetrical bell curve. This suggested that something else may be co-eluting along with the 3,4-DHBA product.

To further confirm 3,4-DHBA synthesis, LC/MS was used. The MS was operated in a single ion detection mode set to detect the DHBA-NH4$^+$ adduct ion. As observed from the ion count vs. time plots in FIG. 12, the sample peak coincided with the DHBA 7.5 mM standard. An additional peak was observed immediately adjacent to (on the right hand side) the peak that coincided with the 3,4-DHBA standard. This species appeared to have the same m/z ratio of 138.10 as the DHBA-NH4$^+$ adduct ion and seemed to elute out of the Aminex column around the same time. The proximity of elution and the same m/z ratio suggested that this co-eluting species may be an isomer of 3,4-DHBA. In particular, 2,3-DHBA is one such isomer that could be formed due to a Type II Claisen condensation reaction. It was hypothesized that this second peak could thus potentially correspond to 2,3-DHBA-NH4$^+$.

3,4-DHBA standard on acid treatment results in lactonization with elimination of water to give 3-hydroxybutyrolactone (3-HBL) resulting in an equilibrium ratio of [3-HBL]/[3,4-DHBA]=2. However, when the 3,4-DHBA from the LC traces was quantified, assuming that the entire peak is attributable to 3,4-DHBA, and these samples were treated with acid, the [3-HBL]/[3,4-DHBA]=0.6. This is clearly much lower than that observed for the standard under similar conditions, indicating that the entire peak is not composed only of 3,4-DHBA but rather, the observed peak is composed of 3,4-DHBA and something else that was co-eluting around the same time as 3,4-DHBA.

Investigating 2,3-DHBA Synthesis with Deuterium Labeled Glycolate

Cells were fed with deuterium labeled glycolate. The structure below shows the labeling positions.

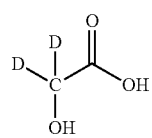

2,2-D2-glycolic acid.

Figure 24:
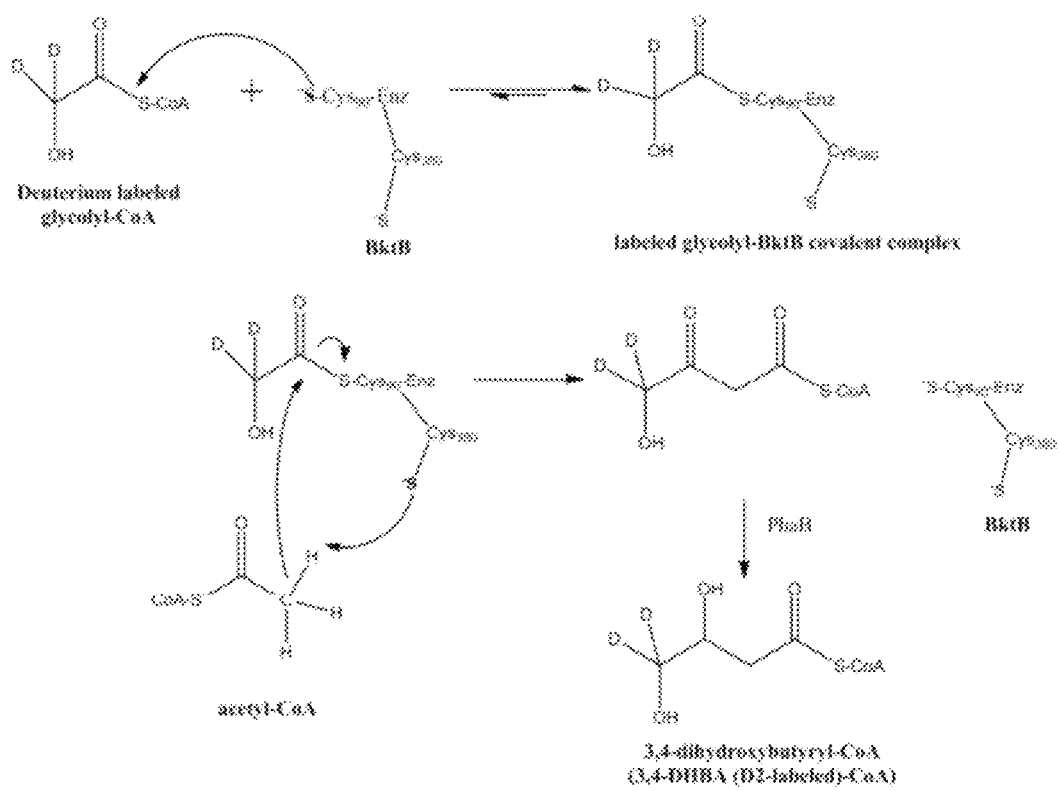
FIG. 24 shows a mechanism for formation of 3,4-DHBA (D2-labeled).
Figure 25:
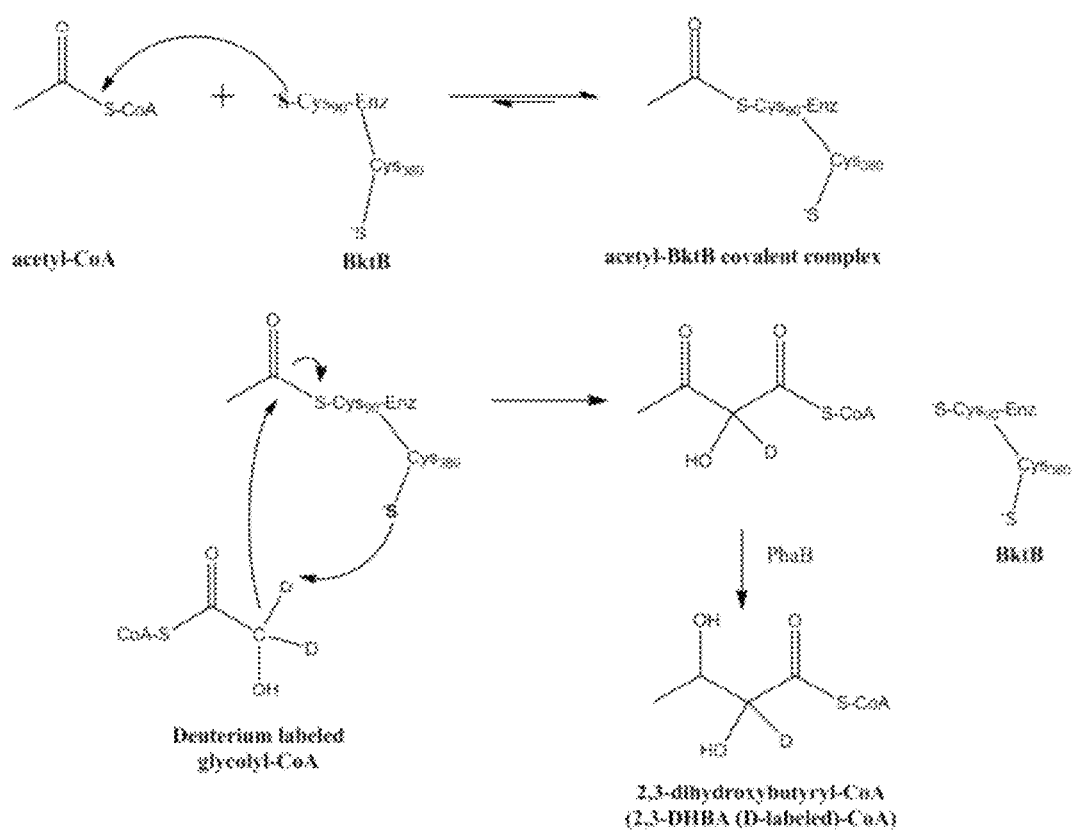
FIG. 25 shows a mechanism for formation of 2,3-DHBA (D-labeled).
Figure 26:
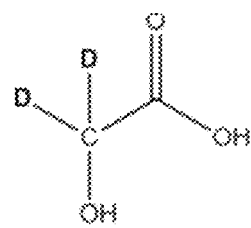
FIG. 26 shows chemical structures.
Figure 26:
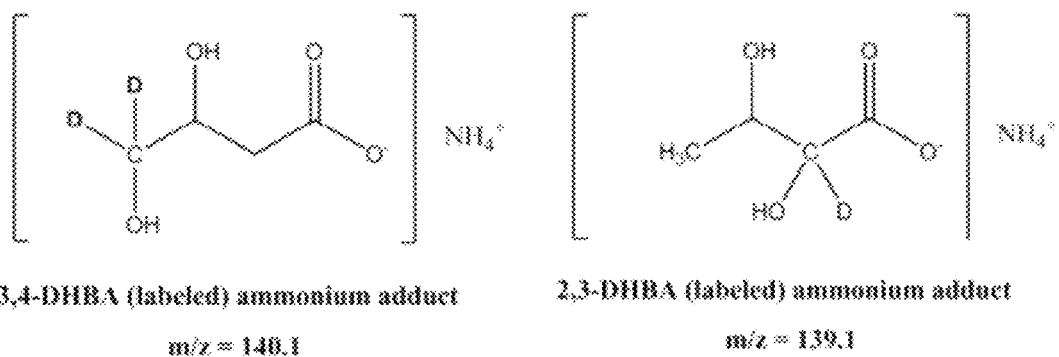

As observed from the structure above, the hydrogens connected to the alpha-carbon atom in glycolic acids were replaced with deuterium. This deuterium labeled glycolate was fed to cells expressing the 3,4-DHBA pathway enzymes Pct, BktB, PhaB and TesB. Culture supernatants after t=72 hrs were analyzed on the LC/MS. The two expected products for this labeled glycolate with their respective mechanisms of formation followed by the structures of the corresponding ammonium adduct products and their m/z ratios are shown in FIGS. 24 and 25.

Figure 12:
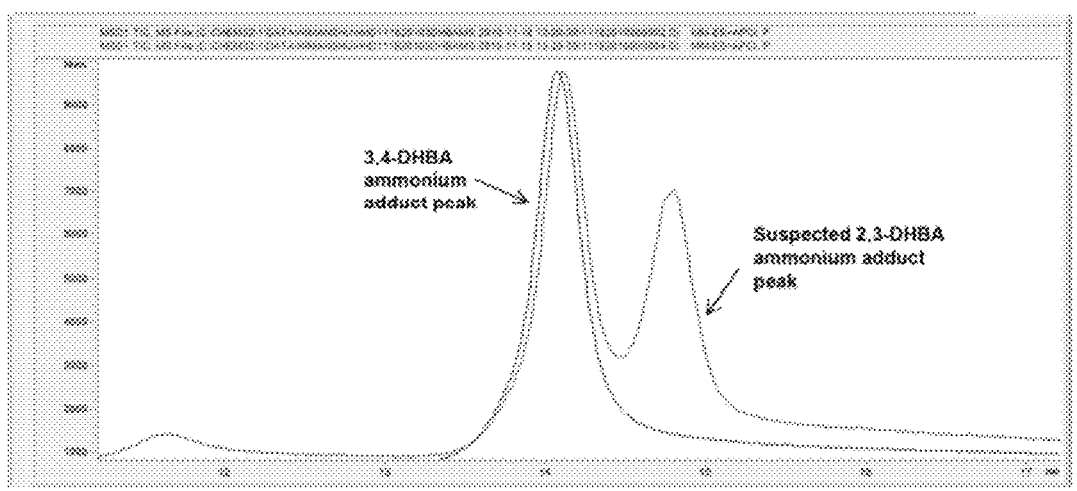
FIG. 12 presents a plot of ion count vs time for day 4 sample for cells fed with glycolate and 7.5 mM DHBA standard.
Figure 13:
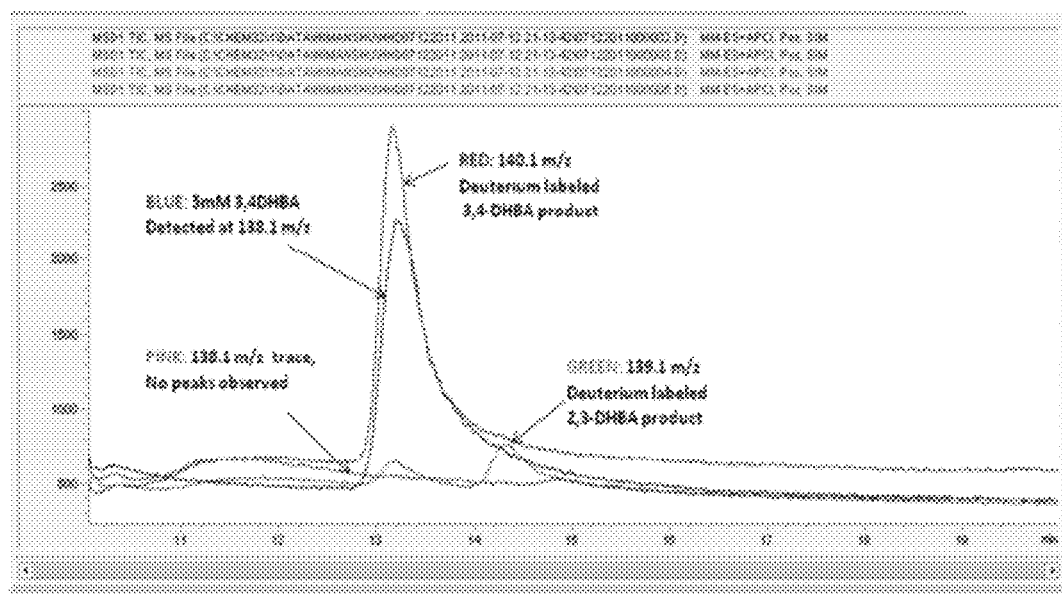
FIG. 13 presents superimposed LC/MS time traces for culture supernatant from a deuterium labeled glycolate fed culture.
Figure 14:
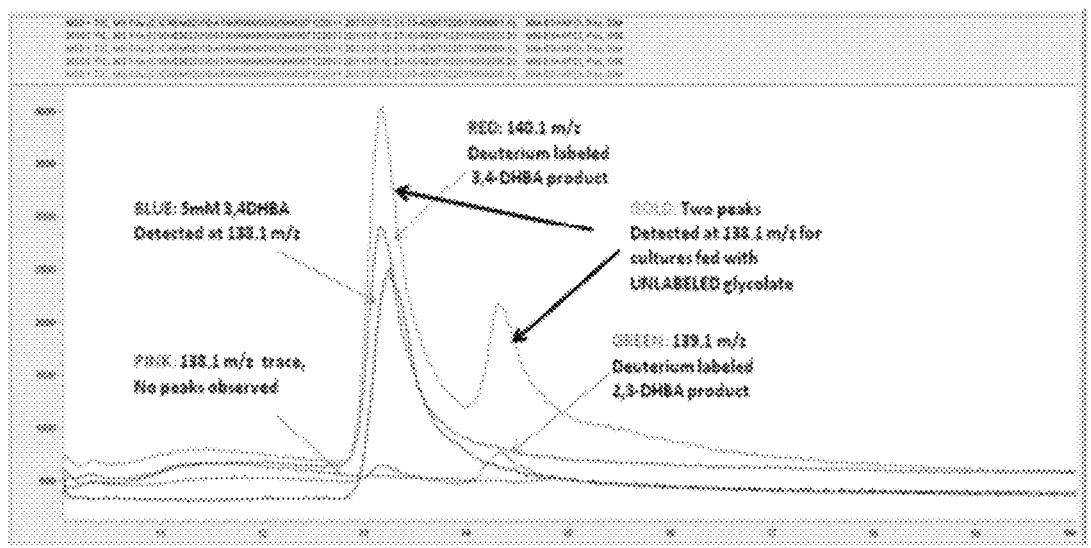
FIG. 14 presents superimposed LC/MS time traces for culture supernatant from a deuterium labeled glycolate fed culture, with an LC/MS trace for cells fed with unlabeled glycolate additionally superimposed.

Because the formation of the 2,3-DHBA (labeled) product involves abstraction of a deuterium, it in fact differs in its m/z ratio from the 3,4-DHBA (labeled) (m/z=140.1) product and would be expected to be detected in the single ion detection mode at m/z=139.1. Indeed, as observed from the LC/MS time trace shown in FIG. 13, cells fed with the deuterium labeled glycolate seemed to make both products, as observed from the superimposed time traces. FIG. 13 shows plots for a deuterium labeled glycolate fed culture supernatant sample analyzed on the LC/MS at three different m/z values in the single ion detection mode: m/z=140.1, m/z=139.1, m/z=138.1 and a control corresponding to the 3,4-DHBA (unlabeled) standard. The peak detected at m/z=140.1 coincides with the 3,4-DHBA standard peak detected at m/z=138.1, indicating that this peak indeed corresponds to the 3,4-DHBA (labeled product). Two additional smaller peaks were observed at m/z=139.1, the second of which (after 14 mins) coincided with the suspected 2,3-DHBA peak observed at the same position for flasks fed with unlabeled glycolate as seen in FIGS. 11 and 12. It was concluded that this peak corresponded to the 2,3-DHBA (labeled) product formed due to the reverse condensation reaction between labeled glycolyl-CoA and acetyl-CoA.

Additionally, flasks fed with unlabeled glycolate were run as controls. As earlier, supernatants from these flasks showed two peaks when analyzed on the MS at m/z=138.1 (FIG. 12). While the first peak was observed to align with the unlabeled 3,4-DHBA standard, the second peak was observed to align with the 2,3-DHBA (labeled) product, providing evidence that indeed BktB could bring about the condensation reaction either way. The observation that the peak for 2,3-DHBA (labeled) was smaller than that for 2,3-DHBA (unlabeled) may be due to a greater difficulty in abstraction of deuterium or slower catalysis with the deuterium intermediate.

Confirming 2,3-DHBA Synthesis Via NMR

To obtain enough material for NMR (about 5 mg), preparative chromatography with the Aminex column was used. MG1655(DE3) ΔendA ΔrecA cells carrying pathway plasmids capable of expression of Pct, BktB, PhaB and TesB were grown in M9 medium supplemented with 1% glucose. The cultures were induced with 100 μM IPTG and culture supernatants were collected after 96 hrs. The pH of the culture supernatants was about 5.5 and was adjusted to about 7 (to prevent acidification on evaporation of water which can result in conversion of 3,4-DHBA to 3-HBL). The water from the supernatant was evaporated using a steady stream of nitrogen blown over the surface to concentrate the culture supernatant from a volume of about 40 ml down to 1.6 ml. This concentrated solution was then repeatedly injected onto the Aminex column (50 separate 30 min runs) and the fraction expected to contain DHBAs (determined by collecting different fractions at 1 min intervals after injection of a DHBA standard) was collected. The different fractions were combined, the pH was adjusted back to close to neutral (between 7 and 8) from pH=2 for the sulfuric acid mobile phase and the water was again evaporated, this time completely to obtain dry residue of pure 2,3-DHBA and 3,4-DHBA. The dry residue was then resuspended in 0.75 mL of $D_2O$. The sample was reanalyzed on the HPLC to confirm that the two DHBAs had indeed been obtained in a pure form. This confirmed that DHBAs had been purified, except for an unknown impurity that was carried forward during the purification. This also allowed quantification of DHBA. About 4.5 mg of the DHBAs (combined) was obtained. Most of this is expected to be 2,3-DHBA as much of the 3,4-DHBA is expected to be lactonized to 3-HBL due to evaporation of water (despite the pH being adjusted to close to neutral). 3-HBL has a boiling point of 104° C. and as a result, in some embodiments, 3-HBL that is formed is expected to evaporate off with water. The resulting sample was analyzed using NMR, confirming the presence of both 2,3-DHBA and 3,4-DHBA.

Advantages and Improvements Over Existing Methods

The established 3-hydroxyalkanoic acid synthesis pathway WO/2010/101651 (Martin et al.) allows synthesis of 3-hydroxyalkanoic acids by feeding small acid molecules via Type I Claisen condensation reaction between the corresponding activated small acid molecules and acetyl-CoA catalyzed by thiolases like BktB. This pathway allows for the synthesis of 3-hydroxyvalerate, 3-hydroxyhexanoate and 4-methyl-3-hydroxy-valerate by feeding propionate, butyrate and isobutyrate respectively. Type II Claisen condensation reaction observed with BktB as a thiolase may be effectively used to synthesize additional 3-hydroxyalkanoic acids that would not be able to be synthesized via a simple direct condensation reaction. In this sense, the present invention is expected to enhance the versatility of the earlier established 3-hydroxyacid synthesis pathway towards synthesis of a vast array of 3-hydroxyalkanoic acids as value added products. The activity demonstrated by BktB is also likely to be also demonstrated by other thiolase enzymes that may exhibit a higher propensity towards the reverse condensation reaction or may be selectively engineered for enhanced reverse condensation activity for synthesis of specific value added products.

3-hydroxyalkanoic acids are valuable chiral molecules that can serve as pharmaceutical building blocks, chiral precursors as well as valuable monomers for biodegradable polymers in the form of polyhydroxyalkanoates. Biodegradable polymers currently employ 3-hydroxybutyrate and 3-hydroxyvalerate due to the ease of synthesis of these acids. The properties of the resulting polymers are restricted by this limited choice of monomers. Alternative 3-hydroxyacids with different carbon chain lengths, substituents and structures can serve as excellent monomers for altering and fine tuning polymer properties by forming co-polymers.

EQUIVALENTS

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

Those skilled in the art will recognize, or be able to ascertain using no more than routine experimentation, many equivalents to the specific embodiments of the invention described herein. Such equivalents are intended to be encompassed by the following claims. All references, including patent documents, disclosed herein are incorporated by reference in their entirety, particularly for the disclosure referenced herein.

What is claimed is:

1. An isolated cell that overexpresses a ycdW gene encoding a glyoxylate reductase enzyme, an aceA gene encoding an isocitrate lyase enzyme, and an aceK gene encoding an isocitrate dehydrogenase kinase/phosphatase enzyme, and that recombinantly expresses a pct gene encoding a propionyl-CoA transferase enzyme, at least one of a phaA, thil, atoB or bktB gene encoding a thiolase enzyme, at least one of a phaB or hbd gene encoding a reductase enzyme, and a tesB gene encoding a thioesterase B enzyme, wherein the isolated cell can produce a cell culture that contains at least $0.1$ g $L^{-1}$ 2,3-dihydroxybutyrate (2,3-DHBA).

2. The isolated cell of claim 1, wherein the isolated cell has reduced or eliminated expression of an iclR gene, an aceB gene and a gcl gene relative to a wild type cell.

3. The isolated cell of claim 1, wherein overexpression of ycdW, aceA and aceK, and recombinant expression of pct, at least one of phaA, thil, atoB or bktB, at least one of phaB or hbd, and tesB, is induced through at least two independently inducible expression systems.

4. The isolated cell of claim 1 wherein the isolated cell is a bacterial cell, a fungal cell, a plant cell, an insect cell or an animal cell.

5. The isolated cell of claim 1, wherein the isolated cell endogenously expresses one or more of ycdW, aceA, and aceK, and wherein endogenous expression of one or more of ycdW, aceA, and aceK is increased through modification of one or more of the gene(s), their promoter(s) and their ribosome binding sites (RBSs).

6. The isolated cell of claim 1, wherein one or more of ycdW, aceA, aceK, pct, phaA, thil, atoB, bktB, phaB, hbd and tesB is expressed from a plasmid, or wherein one or more copies of ycdW, aceA, aceK, pct, phaA, thil, atoB, bktB, phaB, hbd and tesB is integrated into the genome of the isolated cell.

7. The isolated cell of claim 1, wherein one or more of the ycdW, aceA aceK and tesB gene(s) is an *Escherichia coli* gene.

8. The isolated cell of claim 1 wherein one or more of the phaA, bktB and phaB gene(s) is a *Ralstonia eutropha* gene.

9. The isolated cell of claim 1 wherein the pct gene is a *Megasphaera elsdenii* gene.

10. A method for producing 2,3-DHBA comprising culturing the isolated cell of claim 1 to produce 2,3-DHBA, optionally wherein the method further comprises recovering the 2,3-DHBA from the cell culture.

11. A cell culture produced by culturing the isolated cell of claim 1, wherein the cell culture contains at least $0.1$ g $L^{-1}$ 2,3-DHBA.

12. A supernatant of a cell culture produced by culturing the isolated cell of claim 1, optionally wherein the supernatant is subjected to lactonization and optionally wherein lactonization is achieved through acidification to reduce the pH of the supernatant.

13. The method of claim 10, wherein the isolated cell is a bacterial cell, a fungal cell, a plant cell, an insect cell or an animal cell.

14. The method of claim 10, wherein the isolated cell endogenously expresses one or more of ycdW, aceA, and aceK, and wherein endogenous expression of one or more of ycdW, aceA, and aceK is increased through modification of the gene(s) and/or their promoter(s) and/or their ribosome binding sites (RBSs).

15. The method of claim 10, wherein one or more of ycdW, aceA, aceK, pct, phaA, thil, atoB, bktB, phaB, hbd and tesB are expressed from a plasmid, or wherein one or more copies of ycdW, aceA, aceK, pct, phaA, thil, atoB, bktB, phaB, hbd and tesB is integrated into the genome of the cell.

16. The method of claim 10, wherein one or more of the ycdW, aceA, aceK, and tesB gene(s) is an *Escherichia coli* gene.

17. The method of claim 10, wherein one or more of the phaA, bktB and phaB gene(s) is a *Ralstonia eutropha* gene.

18. The method of claim 10, wherein the pct gene is a *Megasphaera elsdenii* gene.

19. A cell culture produced by the method of claim 10, wherein the cell culture contains at least $0.1$ g $L^{-1}$ 2,3-DHBA.

20. A supernatant of a cell culture produced by the method of claim 10, optionally wherein the supernatant is subjected to lactonization and optionally wherein lactonization is achieved through acidification to reduce the pH of the supernatant.

21. The isolated cell of claim 4 wherein the cell is a yeast cell.

22. The method of claim 13, wherein the isolated cell is a yeast cell.

* * * * *